(12) United States Patent
Wach et al.

(10) Patent No.: US 9,744,184 B2
(45) Date of Patent: Aug. 29, 2017

(54) TREHALULOSE-CONTAINING COMPOSITION, ITS PREPARATION AND USE

(75) Inventors: Wolfgang Wach, Worms (DE); Thomas Rose, Worms (DE); Michael Klingeberg, Grünstadt (DE); Siegfried Peters, Biblis (DE); Tillmann Dörr, Hohen-Sülzen (DE); Stephan Theis, Deidesheim (DE); Jörg Kowalczyk, Eisenberg-Steinborn (DE); Stephan Hausmanns, Mannheim (DE)

(73) Assignee: SUDZUCKER AKTIENGESELLSCHAFT MANNHEIM/OCHSENFURT (DE)

( * ) Notice: Subject to any disclaimer, the term of this patent is extended or adjusted under 35 U.S.C. 154(b) by 0 days.

(21) Appl. No.: 13/263,361

(22) PCT Filed: Apr. 15, 2010

(86) PCT No.: PCT/EP2010/002308
§ 371 (c)(1),
(2), (4) Date: Dec. 6, 2011

(87) PCT Pub. No.: WO2010/118866
PCT Pub. Date: Oct. 21, 2010

(65) Prior Publication Data
US 2012/0070386 A1     Mar. 22, 2012

Related U.S. Application Data

(63) Continuation-in-part of application No. 12/386,187, filed on Apr. 15, 2009, now abandoned.

(51) Int. Cl.
| | |
|---|---|
| A01N 43/04 | (2006.01) |
| A61K 31/7016 | (2006.01) |
| C12P 19/12 | (2006.01) |
| C12P 19/18 | (2006.01) |
| C12P 39/00 | (2006.01) |
| A23L 27/30 | (2016.01) |
| A23L 33/10 | (2016.01) |
| A23L 33/20 | (2016.01) |

(52) U.S. Cl.
CPC .......... *A61K 31/7016* (2013.01); *A23L 27/33* (2016.08); *A23L 33/10* (2016.08); *A23L 33/20* (2016.08); *C12P 19/12* (2013.01); *C12P 19/18* (2013.01); *C12P 39/00* (2013.01)

(58) Field of Classification Search
None
See application file for complete search history.

(56) References Cited

U.S. PATENT DOCUMENTS

| | | | |
|---|---|---|---|
| 5,229,276 A | 7/1993 | Sugitani et al. | |
| 6,146,856 A | 11/2000 | Heikkila et al. | |
| 8,148,350 B2 | 4/2012 | van Laere et al. | |
| 2005/0002988 A1 | 1/2005 | Mizumoto et al. | |
| 2007/0026110 A1 | 2/2007 | Baldwin et al. | |
| 2007/0178217 A1* | 8/2007 | Ebashi ......................... 426/598 |
| 2009/0143277 A1 | 6/2009 | Mizumoto et al. | |
| 2009/0221525 A1 | 9/2009 | Coy et al. | |
| 2010/0330234 A1 | 12/2010 | Kowalczyk et al. | |

FOREIGN PATENT DOCUMENTS

| | | |
|---|---|---|
| CA | 1110189 | 10/1981 |
| EA | 017724 B1 | 2/2013 |
| EP | 0 091 063 B1 | 10/1983 |
| EP | 0 483 755 A2 * | 5/1992 |
| EP | 0 625 578 B1 | 11/1994 |
| EP | 0 794 259 B1 | 9/1997 |
| EP | 1 393 637 A1 | 3/2004 |
| EP | 1 424 074 A1 * | 6/2004 |
| EP | 0 983 374 B1 | 11/2005 |
| JP | 54-95791 | 7/1979 |
| WO | WO 2007/107295 A1 | 9/2007 |
| WO | WO 2010/069580 A1 * | 6/2010 |

OTHER PUBLICATIONS

Nagai et al (Biosci Biotech Biochem, 1994, 58(10): 1789-1793).*
Allegri et al (Food Chemistry, 1993, 47(1): Abstract).*
Ravaud et al (JBC, 2007, 282: 28126-28136).*
Allegri et al (Food Chemistry, 1993, 47(1): 23-27).*
Arai et al (Metabolism Clinical and Experimental, 2007, 56: 115-121).*
Office Action dated Dec. 7, 2012 in corresponding Chinese Patent Application No. 201080023895.0 (with English language translation).
International Search Report dated Sep. 29, 2010, issued in corresponding international application No. PCT/EP2010/002308.
Yukie Nagai, et al. "Characterization of α-Glucosyltransferase from *Pseudomonas Mesoacidophila* MX-45," Biosci. Biotech. Biochem., vol. 58, No. 10, pp. 1789-1793 (1994).
Moez Rhimi et al., "Bacterial Sucrose Isomerases: Properties and Structural Studies" Biologica, vol. 63, No. 6, pp. 1020-1027 (2008).
Sumio Kitahata, et al., "Production and Properties of Oligosaccharides Synthesized From Sucrose," Glycoenzymes, pp. 227-239 (2000).
Chinese Office Action dated Jul. 8 2013 in corresponding Chinese Patent Application No. CN 201080023895.0 with English language translation.
Xiaojuan Liu, et al., "The Function of Trehalose and its Application in Food," Food and Nutrition in China, Jan. 28, 2008, vol. 1 (with partial English language translation) (3 pages).
Japanese Office Action dated Oct. 29, 2013 issued in corresponding Japanese Patent Application No. 2012-505089 (with English language translation).
Nagai, Y, et al., "Isolation and Utilization of Trehalulose-producing Bacteria," Proceedings of the Research Society of Japan Sugar Refineries' Technologists, 2002, 50, pp. 57-66 (with an English language summary).

(Continued)

*Primary Examiner* — Sean Aeder
(74) *Attorney, Agent, or Firm* — Ostrolenk Faber LLP

(57) ABSTRACT

The present invention relates to a trehalulose-containing composition, its preparation and use.

16 Claims, 8 Drawing Sheets

(56) References Cited

OTHER PUBLICATIONS

Nagai, Y., et al., "Practical Approach to Trehalulose Production Using a Reactor of Immobilized Cells," Food Science and Technology Research, Nippon Shokuhin Kagaku Kogaku Kaishi, 2003, 50(10), pp. 488-492 (with and English language Abstract).

Nakajima, Y., "Manufacture and Utilization of Palatinose," Journal of the Japanese Society of Starch Science, 1988, 35(2), pp. 131-139 (with an English language Abstract).

Eurasian Office Action dated Sep. 24, 2014 in corresponding Eurasian Patent Application No. 201171246/28 (with English language translation).

Kazuhiko Yamada, et al., "Hydrolysis of 1-O-α-D-Glucopyranosyl-D-Fructofuranose (Trehalulose) by Rat Intestinal Sucrase-Isomaltase Complex," Nutrition Reports International, vol. 32, No. 5, Nov. 1985, pp. 1211-1220.

\* cited by examiner

TREHALULOSE-CONTAINING COMPOSITION, ITS PREPARATION AND USE

CROSS REFERENCE RELATED APPLICATIONS

The present application is a 35 U.S.C. §371 National Phase conversion of PCT/EP2010/002308, filed Apr. 15, 2010, which claims benefit of U. S. application Ser. No. 12/386,187, filed Apr. 15, 2009, the disclosure of which is incorporated herein by reference. The PCT International Application was published in the English language.

TECHNICAL FIELD

The present invention relates to a trehalulose-containing composition, that means vitalose, a process for its preparation and methods for the use thereof.

BACKGROUND

Trehalulose (1-O-α-D-glucopyranosyl-D-fructose) and isomaltulose (palatinose, 6-O-α-D-glucopyranosyl-D-fructose) are known structural isomers of sucrose. These isomers are naturally found in honey in small quantities. Both of them are known as non-cariogenic sugars. However, their physical and chemical characteristics are somewhat different, in particular in view of the fact that trehalulose is more soluble in water than isomaltulose with the consequence that their use as food ingredients is different.

Both, isomaltulose and trehalulose, are also known from for instance EP 1 424 074 A1 as being heterodisaccharides, which in comparison to sucrose, show a reduced hydrolysis rate in the small intestine of human or animal consumers, thereby suggesting the provision of nutritional compositions for controlling blood sugar levels, in particular for the use in patients suffering from diabetes and glucose intolerance, or for obesity prevention. However, the document is silent on the specific role and relevance of isomaltulose and trehalulose contained in the nutritional compositions.

EP 0 483 755 B1 discloses processes to prepare compositions comprising trehalulose and isomaltulose. In particular, *Pseudomonas mesoacidophila* MX-45 (FERM-BP 3619) or *Agrobacterium radiobacter* MX-232 (FERM-BP 3620) was used to convert a sucrose containing medium into a primarily trehalulose, but also significant amounts of isomaltulose containing solution. Thus, the disclosed methods make use of the capability of the α-glucosyltransferase of either *Pseudomonas mesoacidophila* or *Agrobacterium radiobacter* to convert sucrose both into trehalulose and isomaltulose, wherein predominantly trehalulose is obtained.

EP 0 794 259 B1 discloses the preparation of a trehalulose-containing polysaccharide composition using a maltose/trehalose converting enzyme from *Pseudomonas putida, Thermus ruber, Thermus aquatica* or *Pimelobacter* to produce the trehalulose-containing composition from a sucrose solution.

EP 0 091 063 A2 discloses a process for the preparation of isomaltulose using immobilized bacterial cells, in particular cells from *Protaminobacter rubrum* (CBS 574.77). The process disclosed therein uses a sucrose-containing solution, which is subjected to these immobilized cells so as to obtain a primarily isomaltulose containing composition, which, however, also comprises trehalulose.

EP 1 393 637 A1 discloses agents for sustaining concentration and attentiveness, in particular food and drinks containing said agents. The document discloses products for human consumption, which are said to improve the concentration and attention due to the presence of isomaltulose contained in the product.

EP 0 983 374 B1 discloses processes for the simultaneous production of isomaltulose and/or trehalulose and betain.

All of these processes aim to produce either a trehalulose or a isomaltulose-containing composition or even pure trehalulose or isomaltulose so as to make use of the known physiological properties, in particular their non-cariogenity and their slow hydrolyses rate in the small intestine. Although isomaltulose is an attractive agent for developing products suitable to prevent and treat overweight, obesity, diabetes and other glucose or insulin metabolism-related conditions and diseases, there still remains the need to provide even more effective active ingredients.

The production of trehalulose-containing compositions, also termed vitalose, which comprise a high content of isomaltulose is for a number of applications, such as jelly or fruit juices, not desirable, since isomaltulose tends to crystallize out, in particular in applications in an aqueous surrounding. Although the preparation of compositions comprising a high content of trehalulose is for some applications advantageous, it has for other applications the disadvantage of its severely inhibited crystallization capability. Up to now there has been no report on processes to obtain trehalulose-containing compositions, that means vitalose, which comprise both trehalulose and isomaltulose in significant amounts, and which allow the production thereof in an easy, inexpensive and commercially suitable way and which provide the advantage of its composition, in particular its ratio of trehalulose to isomaltulose, being adjustable according to the specific needs of the particular application of the produced trehalulose-containing composition, that means vitalose. Furthermore, there is the need in the art to provide improved means and methods for the prophylaxes and treatment of conditions and diseases related to the glucose and/or insulin metabolism in the human or animal body, in particular for specific groups of patients, which up to now have not been considered to be suitable for being supplied with a carbohydrate, in particular sugar-containing diet.

SUMMARY

Thus, the technical problem underlying the present invention is to provide improved trehalulose- and isomaltulose-containing compositions, in the following termed "vitalose" or "trehalulose-containing compositions", which overcome the above-identified disadvantages and which in particular enable advantageous applications, in particular in the prophylaxes and therapy of conditions and diseases related to the glucose and/or insulin metabolism, preferably for specific groups of consumers or patients. Thus, in the context of the present invention the terms "trehalulose-containing composition" and "vitalose" refer to the same trehalulose- and isomaltulose-containing composition and are used interchangeably. The technical problem underlying the present invention is also to provide processes for the production of trehalulose-containing compositions, that means vitalose, in an industrial scale, in particular processes which allow their production in a particularly variable way, i.e. in a way allowing the production of, preferably a preselected, product composition, preferably exhibiting a specific, preferably preselected trehalulose/isomaltulose ratio.

The present invention solves its problem by the teaching of the independent claims.

Thus, in a preferred embodiment the present invention solves its technical problem by providing a process for the preparation of a trehalulose-containing composition, that means vitalose, wherein (a) a sucrose containing composition is contacted under appropriate conditions with cells or cell extracts from microorganisms of the genus *Pseudomonas* and the genus *Protaminobacter* and (b) the trehalulose-containing composition, that means vitalose, is produced.

Thus, the above-identified process of the present invention foresees subjecting a sucrose-containing composition, in particular an agueous medium comprising sucrose, to an enzymatic activity, in particular an α-glucosyltransferase activity, preferably contained in a cell or cell extract, from microorganism of the genera *Pseudomonas* and *Protaminobacter*, for a time period and under conditions suitable to convert the sucrose into a trehalulose-containing composition, that means vitalose. In a preferred embodiment the trehalulose-containing composition, that means vitalose, is isolated and optionally further purified, preferably subsequent to the complete, i.e. 100% conversion, or almost complete, that means at least a 95, 96, 97, 98 or 99% conversion of the sucrose. The obtained trehalulose-containing composition, that means vitalose, may be further purified according to prior art methods and according to the particular needs resulting from the intended application. In a preferred embodiment it is for instance possible to further purify the obtained trehalulose-containing composition, that means vitalose, by chromatography, filtration, deionisation, decolouration, enzymatic treatment, catalytic treatment and/or fractionation.

Thus, the present invention provides the advantageous and unexpected teaching that cells or cell extracts from a microorganism of the genus *Pseudomonas* and cells or cell extracts from a microorganism of the genus *Protaminobacter* can be used simultaneously and together in one single process to generate from a sucrose-containing composition a trehalulose-containing composition, that means vitalose, preferably with a preselected and easily adaptable composition of its components. Favourably, the present teaching allows to produce a trehalulose-containing composition, that means vitalose, with a broad range of ratios of its components, particularly trehalulose and isomaltulose. In particular, the combined and simultaneous use of cells or cell extracts from both *Pseudomonas* and *Protaminobacter* produces an advantageous composition, in particular sweetener composition, comprising mainly both of trehalulose and isomaltulose, in the following termed "trehalulose-containing composition", that means vitalose, and which provides the advantages detailed below, namely which shows an unexpected glycemic and insulinemic behaviour and opens up further advantageous methods and uses thereof, in particular in controlling body weight and in general glucose and insulin metabolism-related conditions and diabetes. The trehalulose-containing composition, that means vitalose, of the present invention is essentially non-cariogenic, preferably completely non-cariogenic, and has a low glycemic and low insulinemic index. The present composition is a low calorie composition, which is suitable for health oriented consumers and also in particular for diabetics and combines a pleasant sweetening effect with good bodying properties, which advantageously can be prepared in solid form, but also advantageously can be used in form of a syrup, in particular a suspension or in form of a solution. In particular, the composition of the present invention does not crystallize out in the concentrations used. The compositions of the present invention have—without being bound by theory—a composition, attributed mainly by a specific ratio of it various components, in particular the ratio of trehalulose to isomaltulose and to the minor carbohydrate components isomaltose, isomelezitose and oligomers.

DETAILED DESCRIPTION

In the following, reference to percent (%) is a reference to weight-%, unless otherwise specified. In the context of the present invention, all amounts, in particular relative amounts of components of a composition, do not exceed 100%, preferably add up to 100% based either on the dry matter of the composition or the overall weight of the composition, as indicated.

In the context of the present invention, a sucrose-containing composition is preferably a composition comprising 1 to 100%, preferably 1 to 99 weight-% or 90 to 100 weight-% sucrose (weight-% of dry matter). In a particularly preferred embodiment a sucrose-containing composition has a sucrose content of preferably 2, 3, 4, 5, 6, 7, 8, 9, 10, 20, 30, 40, 50, 60, 70 or 80 to 98 weight-%, preferably 3, 4, 5, 6, 7, 8, 9, 10, 20, 30, 40, 50, 60, 70 or 80 to 97 weight-%, preferably 4, 5, 6, 7, 8, 9, 10, 20, 30, 40, 50, 60, 70 or 80 to 96 weight-%, preferably 5, 6, 7, 8, 9, 10, 20, 30, 40, 50, 60, 70 or 80 to 95, 96, 97, 98 or 99 weight-%, preferably 60 to 90 weight-%, preferably 70 to 80 weight-%, preferably 30 to 60 weight-% or preferably 40 to 50 weight-% sucrose (each based on dry matter of the composition). Most preferably, the sucrose content of the sucrose-containing composition is from 90 to 99 weight-%, preferably 90 to 98 weight-% (each based on dry matter of composition).

In a particularly preferred embodiment, the sucrose-containing composition is used in liquid form, particularly is dissolved or suspended in an aqueous medium, preferably is an aqueous sucrose-containing solution or suspension. Preferably, the above-identified sucrose-containing composition may be dissolved or suspended in an aqueous medium, e.g. water, so as to obtain a solution or suspension comprising 0.1 to 80 weight-%, preferably 40 to 75 weight-%, preferably 40 to 60 weight-%, in particular 10 to 60 weight-%, preferably 20 to 55 weight-% of the sucrose-containing composition in water, thus adding up with water or an aqueous medium to 100% (based on overall weight of solution or suspension). In a particularly preferred embodiment the sucrose-containing solution or suspension has a sucrose content of 0.1 to 80 weight-%, preferably 5 to 30 weight-%, 20 to 30 weight-%, 20 to 60 weight-%, 30 to 60 weight-% or 40 to 75 weight-%, preferably 40 to 60 weight-%, in particular 10 to 60 weight %, preferably 20 to 55 weight-% sucrose (based on overall weight of the liquid solution or suspension). In a particularly preferred embodiment the sucrose-containing solution or suspension may also be a thin juice or thick juice from a sugar factory having preferably a dry substance content of 5 to 30%, preferably 20 to 27%. It is also possible to use molasses or other impure sucrose compositions found in sugar factories.

In the context of the present invention a cell or cell extract from a microorganism of the genus *Pseudomonas* is suitable under appropriate conditions to convert sucrose into a composition comprising trehalulose and isomaltulose. In the context of the present invention a cell or cell extract from a microorganism of the genus *Protaminobacter* is suitable under appropriate conditions to convert sucrose into a composition comprising trehalulose and isomaltulose. Thus, in the present invention the cells or cell extracts from the microorganism of the genera *Pseudomonas* and *Protaminobacter* are cells or cell extracts capable of forming trehalulose and isomaltulose from sucrose.

In the context of the present invention a cell extract is meant to be an extract or a part from one or more of the cells of the microorganism used in accordance with the present invention, for instance refers to disrupted cells. In a particularly preferred embodiment the cell extract is also referring to a solution or suspension of an enzyme or enzyme system having the capability to convert sucrose into trehalulose and isomaltulose, in particular is a solution or suspension containing the α-glucosyltransferase from *Pseudomonas* and/or *Protaminobacter*, that means preferably an α-glucosyltransferase or sucrose-6-glucosylmutase (EC 5.4.99.10). Thus, the present invention foresees the use of cells or cell extracts, wherein the term "cell extract" in a preferred embodiment also means enzymes, this term also including enzyme systems, comprising said α-glucosyltransferase. According to the invention it is possible to use whole or disrupted cells of the microorganism with the cells acting as carrier for the enzyme system. The cells, in particular the immobilized cells, are preferably dead. The enzyme or enzyme system used according to the present invention can be extracted from cells from the microorganism by conventional techniques, for example by solvent extraction, French press, lyophilisation and/or enzymatic treatment. It is possible to use auxiliary processes to facilitate extraction, such as disrupting the cells or osmotic shocking. The extracted enzyme or enzyme system may be purified further or may be used as it is. The present invention not only foresees the use of the naturally occurring wild type enzymes, that means the α-glucosyltransferase, from *Pseudomonas* and/or *Protaminobacter*, but also foresees to use genetically engineered derivatives thereof as well as cells from genetically engineered mutants of *Pseudomonas* and/or *Protaminobacter*.

In a particularly preferred embodiment of the present invention, the microorganism of the genus *Pseudomonas* is a microorganism of the species *Pseudomonas mesoacidophila*, preferably is *Pseudomonas mesoacidophila* MX-45, preferably *P. mesacidophila* MX-45 (FERM-BP 3619, said organism is disclosed for instance in EP 0 483 755 B1 or EP 0 625 578 B1 deposited also under FERM 11808) or also publically available from Nagai et al. (Biosc. Sci. Biotech. Biochem. 58 (10), (1994) 1789-1793)). In a particularly preferred embodiment of the present invention the microorganism of the genus *Protaminobacter* is a microorganism of the species *Protaminobacter rubrum*, preferably is *Protaminobacter rubrum* CBS 574.77 (*Protaminobacter rubrum* CBS 574.77 is for instance described in EP 0 091 063 A2 or EP 0 625 578 B1).

The appropriate conditions for converting the sucrose-containing composition into the trehalulose-containing composition, that means vitalose, are in a preferred embodiment a temperature of 10° C., preferably 15° C. to 40° C., preferably 10° C. to 37° C., preferably 25° C. to 40° C., preferably 30° C. to 40° C., preferably 10° C. to 25° C., preferably 15° C. to 30° C., 18° C. to 26° C. and most preferably 10° C. to 20° C., and particularly preferred 10 to 17° C.

In a furthermore preferred embodiment the process is carried out at a pH value from 5.0 to 9.0, preferably 5.0 to 7.0, preferably 6.0 to 7.0.

In a furthermore preferred embodiment the sucrose-containing composition is subjected to the cells or cell extracts from the genera from the microorganisms *Protaminobacter* and *Pseudomonas* for a time period and under conditions suitable to achieve a conversion of sucrose to the trehalulose-containing composition, that means vitalose, of 20 to 100%, preferably 30 to 95, 96, 97, 98, 99% and preferably 100%, preferably 40 to 98%, preferably 50, 60 or 70 to 97%, preferably 50, 60, 70 or 80 to 98%, preferably 75 to 98%, most preferably 50 to 99%, most preferably 60 to 98%, 85 to 100% and preferably more than 95, 96, 97, 98 or 99% (based on amount of sucrose). Most preferably, the obtained trehalulose-containing composition, that means vitalose, is essentially free of sucrose, preferably is free of sucrose.

In a preferred embodiment of the present invention the cells, which may be living or dead, or the cell extract may be used in non-immobilized form. In a furthermore preferred embodiment the cells or the cell extracts, in particular the enzymes, are immobilized on at least one carrier, preferably on two different types of carriers. In accordance with this preferred embodiment one carrier immobilizes the cell or cell extract from the microorganism of the genus *Pseudomonas* and the other different carrier immobilizes the cells or cell extract from the microorganism of the genus *Protaminobacter*.

In a particularly preferred embodiment the cells or cell extracts from the microorganisms of the genera *Pseudomonas* and *Protaminobacter* are co-immobilized on the same carrier. Thus, in this embodiment one and the same carrier, i.e. preferably one type of carrier particles, do contain both cells or cell extracts combined on or in the carrier.

The immobilization can be carried out using prior art technologies. Preferably, the present invention foresees to use entrapment within a gel. Cells can preferably also be physically adsorbed on an inner support. They may preferably also be covalently coupled to an inner support or they can be aggregated by use of a cross-linking agent. According to the present invention, entrapment in a gel is preferred.

Suitable gel materials may be alginate, polyacrylamide, agar, xanthan gum/locust bean gum, kappacarrageenan or kappacarrageenan/locust bean gum, collagen or cellulose acetate.

In a preferred embodiment, the present invention foresees to use immobilization of the cells or cell extracts in an alginate carrier, in particular a calcium alginate. A preferred immobilization produces an inert three-dimensional polymer network, providing a high inward diffusion of sucrose and a high stability. To prepare in a preferred embodiment the immobilized cells or cell extracts, preferably in an alginate gel, the cells or the cell extracts, preferably of both genera of microorganisms together, are mixed with an aqueous solution of a soluble alginate, for instance sodium alginate. In a preferred process this will involve slurrying the whole cells or disrupted cells, i.e. cell extracts, with a soluble alginate. In a preferred embodiment, the concentration of cells is between 1 and 90 weight-% of the solution, preferably 10 to 40 weight-%, preferably 20 weight-% (each net weight (volume)) of the solution. The resultant alginate mixture is then metered into a solution of a metal salt with which the soluble alginate forms a gel, for instance a calcium alginate produced by using calcium chloride. It is also possible to immobilize the microorganisms of the genus *Pseudomonas* separately from the microorganisms of the genus *Protaminobacter* and mix the both separately immobilized microorganisms at a later stage before the sucrose conversion starts.

By metering the slurry or other alginate mixture as discrete droplets it is in a preferred embodiment possible to produce spherical pellets of gel entrapping the cells or cell extracts. Preferably the pellet size can be varied, wherein pellets having a size of 3 to 5 diameter are preferred. In a furthermore preferred embodiment it is also possible to immobilize the cells or cell extracts in a block of gel, a rope of gel or in microfibrous particles. It is also possible to adsorb cells or cell extracts on DEAE-cellulose or by crosslink the cells or cell extracts, for instance with glutaraldehyde.

In a particularly preferred embodiment of the present invention it is foreseen to employ in the process of the present invention a specific ratio, in particular ratio of enzymatic activities or weight ratio of the cells or cell extracts, of *Pseudomonas* and *Protaminobacter*. In a particularly preferred embodiment a process for the production of a trehalulose-containing composition, that means vitalose, is provided wherein the weight ratio or enzymatic activity ratio of cells or cell extracts of *Pseudomonas* to *Protaminobacter* is from 10:1 to 1:10, in particular from 8:1 to 1:8, from 5:1 to 1:5, from 3:1 to 1:3, from 2:1 to 1:2 and in particular is 1:1. In a furthermore preferred embodiment of the present invention a process for the production of trehalulose-containing composition, that means vitalose, is provided, wherein the ratio of weight or enzymatic activity of *Pseudomonas* to *Protaminobacter* is from 10:1 to 1.1:1, 8:1 to 1.1:1, 5:1 to 1.1:1, 3:1 to 1.1:1, preferably from 2:1 to 1.1:1. In a furthermore preferred embodiment of the present invention a process for the production of trehalulose-containing composition, that means vitalose, is provided, wherein the ratio of weight or enzymatic activity of *Pseudomonas* to *Protaminobacter* is from 1:1.1 to 1:10, 1:1.1 to 1:8, 1:1.1 to 1:5, 1:1.1 to 1:3, 1:1.1 to 1:2. In a particularly preferred embodiment a process is provided according to the above, wherein the ratio of weight or enzymatic activities of cells or cell extracts from *Pseudomonas* to *Protaminobacter* is different from a 1:1 ratio, in particular, wherein the ratio is greater than 1, that means>1:1 or is smaller than 1 that means<1:1.

A process in accordance with the present invention is preferably carried out as a continuous process, a discontinuous process, preferably in batch wise operation or a semi-continuous process. The process may preferably be carried out in a fixed bed reactor. The process may preferably be carried out in a reaction vessel, a biofermentor or a tank, preferably under mechanical agitation.

In one further embodiment the immobilized cells or cell extracts are loaded into a column and the substrate, i.e. the sucrose-containing solution or suspension is passed through the column so as to harvest the trehalulose-containing composition in the flow-through. Preferably several columns may be employed in parallel, for example on a carrousel.

The present invention also provides a trehalulose-containing composition, that means vitalose, comprising trehalulose and isomaltulose, in particular obtained or being obtainable according to any one of the preceding processes. In particular, the combined and simultaneous use of cells or cell extracts from the microorganism of the genera *Pseudomonas* and *Protaminobacter* converts the sucrose-containing composition favourably in a specific trehalulose-containing composition, that means vitalose. Said composition, which is a natural, essentially non-cariogenic, low insulinemic and low glycemic sweetener composition, provides the physiologically advantageous properties as disclosed therein and simultaneously provide a sucrose-like temporal and flavour profile, which is not found in compositions comprising isomaltulose or trehalulose each alone. Preferably, the trehalulose-containing composition, that means vitalose, of the present invention is used in a liquid form, in particular in form of a syrup, which advantageously in a particularly preferred embodiment does not crystallize out. Trehalulose and the trehalulose-containing composition, that means vitalose, of the present invention have a good solubility in aqueous media, which enables a particularly wide range of applications.

In the context of the present invention a trehalulose-containing composition, that means vitalose, of the present invention is a composition, which primarily comprises trehalulose and isomaltulose and which comprises minor components, which are in particular isomaltose, isomelezitose, carbohydrate oligomers with a DP (degree of polymerization) greater or equal to 3, and optionally glucose, fructose and/or sucrose. In one embodiment of the present invention, it is foreseen to remove one, more or all of the minor components, for instance isomaltose, isomelezitose and/or the oligomers. In one embodiment, the sweetener composition of the present invention exhibits a more sucrose-like temporal and/or sucrose-like flavor profile than a sweetener composition comprising trehalulose or isomaltulose each alone. As used herein, the phrases "sucrose-like characteristic," "sucrose-like taste," "sucrose-like sweet," and "sucrose-like" are synonymous and are always understood to relate to sucrose. Sucrose-like characteristics include any characteristic similar to that of sucrose and include, but are not limited to, maximal response, flavor profile, temporal profile, adaptation behavior, mouthfeel, concentration/response function behavior, tastant and flavor/sweet taste interactions, spatial pattern selectivity, and temperature effects. Whether or not a characteristic is more sucrose-like, isomaltulose-like or trehalulose-like is determined by expert sensory panel assessments of sucrose and the compositions comprising trehalulose and/or isomaltulose. Such assessments quantify similarities of the characteristics of compositions comprising trehalulose and/or isomaltulose, with those comprising sucrose.

In a particularly preferred embodiment of the present invention the trehalulose-containing composition, that means vitalose, prepared according to the present invention comprises a trehalulose content suitable to achieve the advantageous physiological properties described herein, in particular the low insulin response induced in the consumer's blood. In a particularly preferred embodiment the trehalulose-containing composition, that means vitalose, of the present invention comprises trehalulose and isomaltulose each in a content that the composition is suitable to achieve the advantageous physiological properties described herein, namely the low insulin response induced in the consumer's blood. In a particularly preferred embodiment of the present invention the product for human or animal consumption of the present invention comprises the trehalulose-containing composition, that means vitalose, of the present invention in an amount suitable to achieve the advantageous physiological properties described herein in the consumer, in particular induces the desired low insulin response in the consumer's blood.

In a particularly preferred embodiment the trehalulose-containing composition, that means vitalose, prepared according to the present invention comprises 20 to 95 weight-%, preferably 30 to 90 weight-%, preferably 25 to 75 weight-%, preferably 40 to 80 weight-% and in particular 30 to 70 weight-%, preferably 35 to 65 weight-%, preferably 45 to 70 weight-% trehalulose (based on dry matter of the composition). Most preferably, the trehalulose-containing composition, that means vitalose, comprises 70 to 80 weight-%, preferably 65 to 78 weight-% trehalulose. Preferably, the remainder of the composition adds up to 100% with isomaltulose, or, optionally isomaltulose and 0.1 to 1, 2, 3 or 4 weight-% of the minor components.

In a furthermore preferred embodiment the trehalulose-containing composition, that means vitalose, of the present invention comprises 8, 10, 20, 30 or 35 to 50 weight-%, in particular 9 to 40 weight-%, preferably 9 to 30 weight-%, preferably 22 to 35 weight-%, preferably 20 to 40 weight-%, preferably 20 to 30 weight-%, preferably 18 to 27 weight-% and most preferably 20 to 25 weight-% isomaltulose (based on dry matter of the composition). Preferably, the remainder of the composition adds up to 100% with trehalulose, or, optionally trehalulose and 0.1 to 1, 2, 3 or 4 weight-% of the minor components.

In a furthermore preferred embodiment of the present invention the trehalulose-containing composition, that means vitalose, of the present invention comprises 0.0, preferably 0.1 to 2.0, 0.1 to 1.5, preferably 0.1 to 1.0, preferably 0.1 to 0.4 weight-% glucose.

In a furthermore, preferred embodiment of the present invention the trehalulose-containing composition, that means vitalose, of the present invention comprises 0.0, preferably 0.1 to 2.0, 0.1 to 1.5, preferably 0.1 to 1.0, preferably 0.1 to 0.4 weight-% fructose.

In a furthermore, preferred embodiment of the present invention the trehalulose-containing composition, that means vitalose, of the present invention comprises 0.0, preferably 0.1 to 2.0, 0.1 to 1.5, preferably 0.1 to 1.0, preferably 0.1 to 0.4 weight-% isomaltose.

In a furthermore, preferred embodiment of the present invention the trehalulose-containing composition, that means vitalose, of the present invention comprises 0.0, preferably 0.1 to 2.0, 0.1 to 1.5, preferably 0.1 to 1.0, preferably 0.1 to 0.4 weight-% isomelezitose.

In a furthermore, preferred embodiment of the present invention the trehalulose-containing composition, that means vitalose, of the present invention comprises 0.0, preferably 0.1 to 2.0, 0.1 to 1.5, preferably 0.1 to 1.0, preferably 0.1 to 0.4 weight-% carbohydrate oligomers, preferably with a DP≥3.

In a particularly preferred embodiment the trehalulose-containing composition, that means vitalose, prepared according to the present invention comprises 70 to 80 weight-% trehalulose and 20 to 30 weight-% isomaltulose. In a particularly preferred embodiment the trehalulose-containing composition, that means vitalose, does not comprise any other components than isomaltulose and trehalulose. In another preferred embodiment the trehalulose-containing composition, that means vitalose, prepared according to the present invention comprises 70 to 80 weight-% trehalulose and 20 to 30 weight-% isomaltulose and one or more of the carbohydrates selected from the group consisting of isomaltose, isomelezitose and carbohydrate oligomers adding up to 100 weight-% from the dry matter of the composition, preferably in a sum of 1 to 6, 1 to 5, 1 to 4 and most preferred 1 to 3 weight-% (based on weight of composition). In a furthermore preferred embodiment the trehalulose-containing composition, that means vitalose, comprises also isomaltose, isomelezitose, glucose, fructose, sucrose and carbohydrate oligomers, preferably in an overall sum adding up to 100 weight-% (DM), preferably in a sum of 1 to 6, 1 to 5, 1 to 4 and most preferred 1 to 3 weight-% (based on weight of composition).

In a preferred embodiment of the present invention it is foreseen to remove one or more of the minor components of the obtained trehalulose-containing composition, that means vitalose, preferably one or more of the group consisting of sucrose, glucose, fructose, isomaltose, isomelezitose and carbohydrate oligomers, most preferably from the group consisting of glucose, fructose and sucrose. In a preferred embodiment said removal may be carried out by methods known in the art, such as filtration, chromatography, for instance anion and/or cation exchange chromatography and enzymatic, for instance invertase, or catalytic cleavage. Preferably, a charcoal and/or resin treatment may be carried out. Thus, in a particularly preferred embodiment it is possible to produce a trehalulose-containing composition, that means vitalose, being free of glucose, fructose and sucrose, which is completely non-cariogenic and provides a particularly low glycemic and insulinemic index.

In a furthermore preferred embodiment of the present invention there is provided a product for human or animal consumption, comprising the trehalulose-containing composition, that means vitalose, of the present invention and at least one additive.

In a preferred embodiment of the present invention the product for human or animal consumption comprises 0.02 to 3.0 weight-%, in particular 0.02 to 1.0 weight-%, preferably 0.02 to 0.5 weight-% of the at least one additive and an amount of the trehalulose-containing composition, that means vitalose, adding up to 100%, in particular 97 to 99.98 weight-%, preferably 99.0 to 99.98 weight-%, in particular 99.5 to 99.98 weight-% of the trehalulose-containing composition, that means vitalose (each based on dry matter). Preferably, the at least one additive contained in the product, preferably in an amount from 0.02 to 3.0 weight-%, is (a) a stevia extract or a steviolglycoside, (b) a stevia extract or a steviolglycoside and at least one of lactobionic acid, lactobionic-δ-lactone, a salt of lactobionic acid or a mixture thereof, or (c) at least one of a lactobionic acid, lactobionic-δ-lactone, a salt of lactobionic acid or a mixture thereof.

In a preferred embodiment of the present invention the product for human or animal consumption comprises 3 to 95 weight-%, preferably 5 to 95 weight-%, preferably 20 to 95 weight-%, preferably 5 to 90 weight-%, preferably 10 to 90 weight-%, preferably 20 to 80 weight-%, preferably 7 to 70 weight-%, most particularly 40 to 60 weight-% of the trehalulose-containing composition, that means vitalose, of the present invention and 5 to 97 weight-%, preferably 5 to 95 weight-%, most preferably 5 to 80 weight-%, preferably the remainder adding up to 100 weight-%, of the at least one additive (each based on dry matter on the overall product).

In a preferred embodiment of the present invention the additive is a high intensity sweetener, preferably is at least one of a stevia extract or a steviolglycoside, in particular a rebaudioside, preferably rebaudioside A (Reb A, CAS no. 58 543-16-1, $C_{44}H_{70}O_{23}$). Most preferred, the trehalulose-containing composition, that means vitalose, of the present invention is present in a product for human or animal consumption together with Reb A as an additive.

For example, particular embodiments may also comprise combinations of steviolglycosides.

Non-limiting examples of suitable steviolglycosides which may or may not be combined include rebaudioside A, rebaudioside B, rebaudioside C, rebaudioside D, rebaudioside E, rebaudioside F, dulcoside A, dulcoside B, rubusoside, stevioside (CAS no. 57817-89-7, $C_{38}H_{60}O_{18}$), or steviolbioside. According to particularly desirable embodiments of the present invention, the combination of high intensity sweeteners comprises rebaudioside A in combination with rebaudioside B, rebaudioside C, rebaudioside E, rebaudioside F, stevioside, steviolbioside, dulcoside A or combinations thereof. For the chemical nomenclature it is referred to the 68th JECFA meeting (2007) published in FAO JECFA Monographs 4 (2007).

In a particularly preferred embodiment a steviolglycoside used as a high intensity sweetener additive according to the present invention is at least one of the group consisting of stevioside, rebaudioside A, rebaudioside C, dulcoside A, rubusoside, steviolbioside and rebaudioside B.

In a particularly preferred embodiment of the present invention the high intensity sweetener used in the present invention is a mixture of Reb A, rebaudioside B, rebaudioside C, dulcoside A, rubusoside, steviolbioside and stevioside, which comprises at least 95 weight-% (based on dry matter of the sweetener composition) of said steviolglycosides.

In a particularly preferred embodiment of the present invention a high intensity sweetener comprising rebaudioside A is used, wherein the rebaudioside A content is at least 97 weight-%, preferably is >97 weight-% of the dry weight of the sweetener composition.

According to a particularly desirable embodiment, the high intensity sweetener comprises a mixture of rebaudioside A, stevioside, rebaudioside B, rebaudioside C, and rebaudioside F; wherein rebaudioside A is present in the mixture of high intensity sweeteners in an amount in the range of about 75 to about 85 weight percent based on the total weight of the mixture of high intensity sweeteners, stevioside is present in an amount in the range of about 1 to about 6 weight percent, rebaudioside B is present in an amount in the range of about 2 to about 5 weight percent, rebaudioside C is present in an amount in the range of about 3 to about 8 weight percent, and rebaudioside F is present in an amount in the range of about 0.1 to about 2 weight percent.

According to particularly preferred embodiments, the purity of the rebaudioside A used may range from about 50% to about 100%; from about 70% to about 100%; from about 80% to about 100%; from about 90% to about 100%; from about 95% to about 100%; from about 95% to about 99.5%; about 96% to about 100%; from about 97% to about 100%; from about 98% to about 100%; and from about 99% to about 100%. According to particularly preferred embodiments, upon crystallization of crude rebaudioside A, the substantially pure rebaudioside A composition comprises rebaudioside A in a purity greater than about 95% by weight up to about 100% by weight on a dry basis. In other preferred embodiments, substantially pure rebaudioside A comprises purity levels of rebaudioside A greater than about 97% up to about 100% rebaudioside A by weight on a dry basis, greater than about 98% up to about 100% by weight on a dry basis, or greater than about 99% up to about 100% by weight on a dry basis.

In a furthermore preferred embodiment of the present invention the additive is at least one of lactobionic acid, lactobionic-δ-lacton, a salt of lactobionic acid or a mixture thereof. According to the present invention the use of these lactobionic acid-based additives provides the advantage of masking or reducing the bitter off-taste of otherwise sweet compounds and provides a sweet flavouring enhancing effect.

Lactobionic acid, lactobionic-δ-lactone, a salt of lactobionic acid or mixtures thereof are thus capable of masking for example bitter flavours. One preferred embodiment of the present invention is a masking of bitter flavours, in particular attributable to stevia extracts or a steviolglycoside, for example rebaudioside A, wherein lactobionic acid, lactobionic-δ-lactone, a salt of lactobionic acid or mixtures thereof are used in combination with the trehalulose-containing composition, that means vitalose, of the present invention and stevia extracts or a steviolglycoside, for instance Reb A, of which it is known that they show a bitter off-taste.

Thus, preferably, the trehalulose-containing composition, that means vitalose, is combined with a stevia extract or a steviolglycoside, particularly a rebaudioside, in particular rebaudioside A, and with another additive, in particular at least one of lactobionic acid, lactobionic-δ-lacton, a salt of lactobionic acid or a mixture thereof.

In a preferred embodiment the product for human or animal consumption therefore comprises the trehalulose-containing composition, that means vitalose, of the present invention and at least two additives, namely a stevia extract or a steviolglycoside, in particular Reb A, and at least one of lactobionic acid, lactobionic-δ-lactone or a salt or mixture thereof. Such a product displays a similar sweetening power than conventional sucrose or sucrose/glucose-based products, but has the physiologically advantageous properties disclosed herein and does not show any unfavourable organoleptic or taste features known to be attributable to conventional artificial sweeteners. In particular, such a product provides a high nutritional and even therapeutical value in combination with a sucrose-like profile of characteristics, in particular sucrose-like taste and sweetness.

The amount of lactobionic acid, lactobionic-δ-lactone, a salt of lactobionic or mixtures thereof that may preferably be incorporated into a food composition in order to benefit from its flavour-enhancing and/or masking properties may vary within wide ranges, and lies preferably between 0.01 wt. % and 90 wt. %, based on the whole of the food composition. Preferably, the amount of lactobionic acid, lactobionic-δ-lactone, a salt of lactobionic acid or mixture thereof that is incorporated into a food composition is at least 0.05, 0.10, 0.25, 0.50, or 1.00 wt. %, based on the whole of the food composition. Preferably the amount of lactobionic acid, lactobionic-δ-lactone, a salt of lactobionic acid or mixture thereof that is incorporated into a food composition is at most 95, 85, 75, 65, 55, 45, 40, 35, 30, 25, 20, 15, or 10 wt. %, based on the whole of the food composition. Dosages of lactobionic acid, lactobionic-δ-lactone, a salt of lactobionic acid or mixtures thereof in amounts of 5 or 10 wt. % to 90 wt. % are often suitable for use in concentrates, table top sweeteners, and salt replacements. Moreover, it was found that the said high dosages of lactobionic acid, lactobionic-δ-lactone, a salt of lactobionic acid or mixtures thereof can be associated with its use as a carrier, for example a carrier of aromas.

If lactobionic acid is used as such, then it may lead to the formation of lactobionic-δ-lactone. In that case, the ratio between lactobionic acid and lactobionic-δ-lactone is determined at least partly by the specific conditions of use. By analogy, the use of lactobionic-δ-lactone as such may lead to the formation of lactobionic acid. The said formation and subsequent presence of lactobionic-δ-lactone or lactobionic acid are understood to be according the use of the present invention.

If a mixture of lactobionic acid, lactobionic-δ-lactone and a salt of lactobionic acid is used in a preferred embodiment then the weight ratio of, one the one hand, the sum of lactobionic acid and lactobionic-δ-lactone to, on the other hand, the salt of lactobionic acid in the mixture, lies preferably between 1:10 and 10:1.

In a furthermore preferred embodiment of the present invention the additive is selected from the group consisting of acidic flavours, fruit flavours, sweet flavours, savoury flavours, salty flavours, a high intensity sweetener, a sugar alcohol, sucromalt, ribose, tagatose, trehalose, organic acid, e.g. citric acid or lactic acid, fruit extracts, a bulk sweetener, a fibre, a prebiotic agent, a thickener, a vitamin, a mineral, a preservative, a fruit preparation, a food colour, a liquid medium, such as water or milk, and a therapeutic agent.

In a furthermore preferred embodiment of the present invention the additive is selected from the group consisting of creatine, polyphenol, L-carnitin, omega-3 polyunsaturated fatty acid, omega-6 polyunsaturated fatty acid, green tea extract, EGCG (epigallocatechingallate), aminoacids and peptopro, which is a pre-digested casein-derived milk protein.

In a further particularly preferred embodiment as a high intensity sweetener aspartame, monellin, brazzeine, cyclamate, neotame, acesulfam K, glycyrrhicine, saccharine, sucralose, alitame, neohesperidine-dihydrochalcone, stevioside, Reb A or thaumatin can be used.

Thus, the trehalulose-containing composition, that means vitalose, may also be combined with an additive, which is at least one sugar alcohol, preferably selected from the group consisting of isomalt, isomalt ST, isomalt GS, mannitol, sorbitol, xylitol, lactitol, erythritol or maltitol.

In a preferred embodiment, as an additive a fibre, preferably a soluble fibre, particularly resistant dextrines, resistant maltodextrines, for instance nutriose, pectine, carrageenan, rice starch, rice syrup, polydextrose, oligosaccharides, for instance galactooligosaccharides or fructooligosaccharides, or fructans, for instance inulin, can be used.

In a furthermore preferred embodiment of the present invention the additive is a tryptophane-containing peptide composition, in particular tryptophane-containing peptides or tryptophane itself. In a preferred embodiment the tryptophane-containing peptide composition comprises at least two different tryptophane-containing peptides, preferably water-soluble peptides. In a particularly preferred embodiment the tryptophane-containing peptides are di- or tripeptides. In a particularly preferred embodiment a food, feed or pharmaceutical product comprising vitalose and the tryptophane-containing peptide composition comprises 0.5 to 5 weight %, preferably 0.9 to 3.5 weight % (dry weight) of the tryptophane-containing peptide composition. In a particularly preferred embodiment of the present invention such a product is particularly useful for improving the mental performance of a subject.

The present invention also provides a product for human and animal consumption which is a food, an animal feed or a pharmaceutical product. The product according to the present invention is preferably a confectionery, a filling for a confectionery, a soft caramel, a hard caramel, a fondant, a yoghurt, a bakery product, a chewing gum, an ice cream, a milk product, a jelly, a beverage, a fruit juice concentrate, a fruit preparation, a marmelade or a smoothie. Preferably, the product is a fruit preparation, a fruit juice, a jelly or a fondant. The beverage may preferably be a beer, a fruit juice, a milk drink, a soft drink, an isotonic drink, a hypertonic drink, a cacao drink, a rice drink, a soya drink, an alcohol free beverage, a beverage with heat- and pH-stable osmolarity, an energy drink or a sport drink.

In a preferred embodiment of the present invention the product for human or animal consumption is a beverage, in particular a beverage comprising at least 1, 2, 3, 4, 5, 6, 7, 8, 9, 10, 20, 30, 40, 50, 60 or 70 weight-% of the trehalulose-containing composition, that means vitalose, optionally including at least one additive, and at most 10, 20, 30, 40, 50, 60, 70, 75 or 80 weight-% (each based on total weight of the beverage) of the trehalulose-containing composition, that means vitalose, optionally including at least one additive, of the present invention the remainder being a liquid medium, in particular an aqueous or milky solution, such as water or milk. In a particularly preferred embodiment the beverage comprises 1 to 30%, preferably 2 to 25%, most preferably 3 to 15% (each based on total weight of the beverage) of the trehalulose containing composition, that means vitalose, optionally including at least one additive, of the present invention the remainder being a liquid medium, in particular an aqueous or milky solution, such as water or milk. Thus, in a preferred embodiment the beverage may contain one or more of the above identified additives, in particular (a) a stevia extract or a steviolglycoside, preferably Reb A, or (b) a lactobionic acid, lactobionic-δ-lacton, a salt of lactobionic acid or a mixture thereof or both of them, that means (a) and (b). In a particularly preferred embodiment of the present invention the trehalulose-containing composition, that means vitalose, of the present invention or a product comprising the trehalulose-containing composition, that means vitalose, of the present invention does not comprise any further sweetening agent except the trehalulose-containing composition, that means vitalose, itself. In a furthermore preferred embodiment of the present invention the trehalulose-containing composition, that means vitalose, of the present invention or a product containing said composition does not comprise any other sugar besides the sugars contained in the trehalulose-containing composition that means vitalose.

In a furthermore preferred embodiment of the present invention the trehalulose-containing composition, that means vitalose, of the present invention or a product containing the trehalulose-containing composition, that means vitalose, of the present invention is free of high intensity sweeteners, is free of sugar replacement agents, such as sugar alcohols, or is free of both. In a particularly preferred embodiment of the present invention the trehalulose-containing composition, that means vitalose, or a product containing said composition is free of sorbitol, is free of mannitol, is free of lactitol, is free of maltitol, is free of xylitol, is free of erythritol or is free of two, three, four, five or all of them.

The present invention also relates to the use of the trehalulose-containing composition, that means vitalose, of the present invention or trehalulose itself for preparing a product for human or animal consumption, which product is capable and designed for a sustained release of glucose and for simultaneously eliciting (herein also called inducing) in a consumer a low blood insulin response, in particular eliciting an insulin response which is significantly lower than elicited by isomaltulose alone.

The present invention also relates to the above-mentioned use, wherein the product is a pharmaceutical product.

The present invention relates to a method for treating a glucose or insulin metabolism-related condition or disease, wherein the product is applied to a subject in need thereof, thereby eliciting a low insulin response and a sustained release of glucose.

The present invention relates to the above method, wherein the glucose or insulin related condition or disease is selected from the group consisting of diabetes, metabolism syndrome, glucose intolerance, insulin resistance, adipositas, obesity, hyperlipidemia, cancer, in particular colon cancer, a liver disease, insulin sensitivity and arthroscleroses.

The present invention is thus also based upon the unexpected finding that trehalulose provides upon uptake by a human or animal consumer in comparison to isomaltulose an increased level of blood glucose and simultaneously elicits a, in comparison to isomaltulose, lower level of insulin in the blood. Thus, although isomaltulose and trehalulose both are low glycemic sugars, trehalulose unexpectedly and advantageously provides the advantage of providing in contrast to isomaltulose a higher level of blood glucose upon ingestion in the human or animal body and simultaneously elicits a lower insulin response, i.e. a lower insulin level in the blood, in contrast to isomaltulose. Thus, trehalulose is a particularly low glycemic agent with a low GI (glycemic index) providing an extremely low insulin response, i.e. provide a very low II (insulin index).

In the context of the present invention a "low insulin response" is an insulin response, which is induced by trehalulose and which is lower than the insulin response induced by isomaltulose. The present invention therefore provides the unexpected teaching that isomaltulose and trehalulose both have a low GI and that trehalulose has a particularly low insulin index (II), meaning provides a low insulin response, i.e. an insulin response lower than that of isomaltulose. The present invention therefore opens up new and advantageous methods and applications for trehalulose and trehalulose-containing compositions, which make use of the above-identified finding. In particular the present invention provides the teaching to use trehalulose or a trehalulose containing composition, that means vitalose, for the preparation of products, in particular for human and animal consumption, which products are designed and suitable for providing a sustained release of glucose and simultaneously elicit only low insulin response, in contrast to a food comprising isomaltulose alone. Thus, a food according to the present invention aims to reduce the level of insulin in the blood and helps to prevent and treat obesity, overweight, adipositas, diabetes mellitus and other glucose and insulin-related diseases or conditions.

Thus, a composition or a food according to the present invention comprising the identified amounts of trehalulose is unexpectedly advantageous in comparison to known compositions, in particular solely or primarily isomaltulose-containing compositions or products, inter alia due to its low insulinemic index. Thus, the present invention provides the technical teaching so as to specifically use and adapt a trehalulose content in a composition, food or method of treatment so as to replace other sweeteners, in particular sucrose, glucose and/or isomaltulose, completely or partially so as to provide a food composition or therapy supplying comparable high amount of glucose and thereby providing a very low insulin response in the consumer's blood. Thus, the present invention provides the advantageous teaching that for a certain level of energy supply a comparable lower insulinemic load is burdened onto the consumer or vice versa that with a certain insulinemic load a higher amount of energy can be supplied to the consumer by using the specific teaching of the present invention, that means the particular properties of trehalulose to provide an extremely low glycemic index and a comparable higher glucose supply to the consumer in contrast to isomaltulose.

The present invention therefore also provides products, uses and methods for treating glucose or insulin metabolism-related conditions or diseases, wherein a product according to the present invention is applied in an amount suitable to achieve the desired effect to a subject in need thereof, in particular a human or animal being thereby eliciting a low insulin response and a sustained release of glucose. In the context of the present invention a glucose or insulin metabolism-related disease is selected from the group consisting of diabetes, in particular diabetes mellitus, type II, metabolism syndrome, glucose intolerance, insulin resistance, insulin sensitivity, adipositas, obesity, hyperlipidemia, cancer, liver diseases, colon cancer and overweight. The present invention provides also the teaching that the use of trehalulose or trehalulose-containing composition, that means vitalose, of the present invention increases the physical and mental performance, increases fat consumption and oxidation, controls the blood glucose and insulin levels, mobilizes free fatty acids and reduces the consumption of glycogen.

The present invention provides the advantageous teaching that trehalulose or the trehalulose-containing compositions, that means vitalose, of the present invention are capable of continuously supplying the body of the consumer, in particular the brain, nerve, blood and muscle cells with glucose for a prolonged and sustained time in a level even higher than provided by isomaltulose while simultaneously, in particular in comparison to isomaltulose, a comparable low insulin response is induced. Thus, the body is provided with a long lasting and continuous energy supply avoiding a reduction in the physical and mental performance and increasing the physical and mental endurance, condition and activity, while reducing the consumption of the glycogen reserves and supporting weight control and weight reduction.

The present invention also relates to a method for the prophylaxes and treatment of tooth diseases, in particular plaque formation or tooth defects, in particular caries, wherein a product or composition of the present invention is applied in an amount suitable to achieve the desired effect to a subject in need thereof. In particular, the present invention, according to which a product or a composition of the present invention is applied to a subject in need thereof, reduces the plaque formation in the mouth of the consumer. Thus, the present invention provides a method for improving the tooth health.

In a furthermore preferred embodiment the present invention relates to a method for improving the mental and/or physical performance, in particular the endurance, wherein a product or composition according to the present invention is applied in an amount suitable to achieve the desired effect to a subject in need thereof. Thus, the present invention provides in a particularly preferred embodiment a method for improving the endurance of a subject in need thereof, whereby in a particularly preferred embodiment the glycogen consumption is reduced.

In a furthermore preferred embodiment the present invention relates to a method for improving, preferably increasing, the fat oxidation of a subject in need thereof, whereby a product or composition according to the present invention is applied in an amount suitable to achieve the desired effect to a subject in need thereof. Furthermore, the present invention relates to a method for the management of body weight, wherein a composition or a product according to the present invention is applied to a subject in need thereof.

In a particularly preferred embodiment the present invention provides a method for reducing the respiratory quotient ($RQ=CO_2$ eliminated/$O_2$ consumed) of a patient, wherein the product or a composition according to the present invention is applied in an amount suitable to achieve the desired effect prior, during or after a physical exercise to the subject in need thereof.

All the methods of using the products and compositions of the present invention can be therapeutic or non-therapeutic methods, for instance relating to cosmetic, activity-related, athletic or life-style orientated methods.

Further preferred embodiments are the subject matter of the subclaims.

BRIEF DESCRIPTION OF THE FIGURES

The invention will now be described by the following examples and the accompanying figures. The figures show.

EXAMPLES

Figure 1:
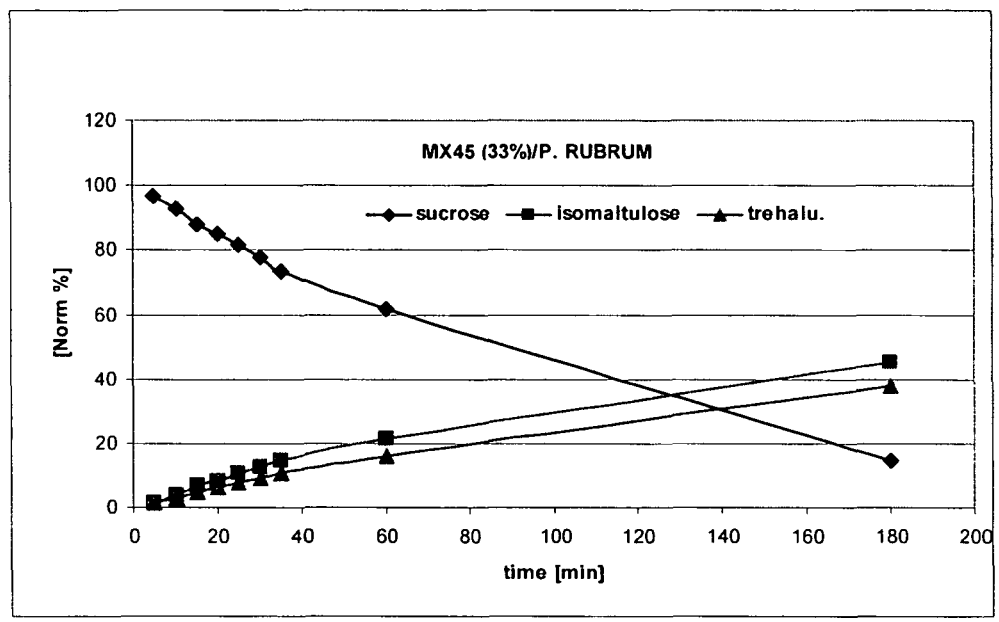
FIGS. 1 to 6 show a graphical presentation of the conversion of a sucrose-containing composition into a trehalulose-containing composition, that means vitalose, of the present invention for various ratios of *Pseudomonas mesacidophila* and *Protaminobacter rubrum*.
Figure 2:
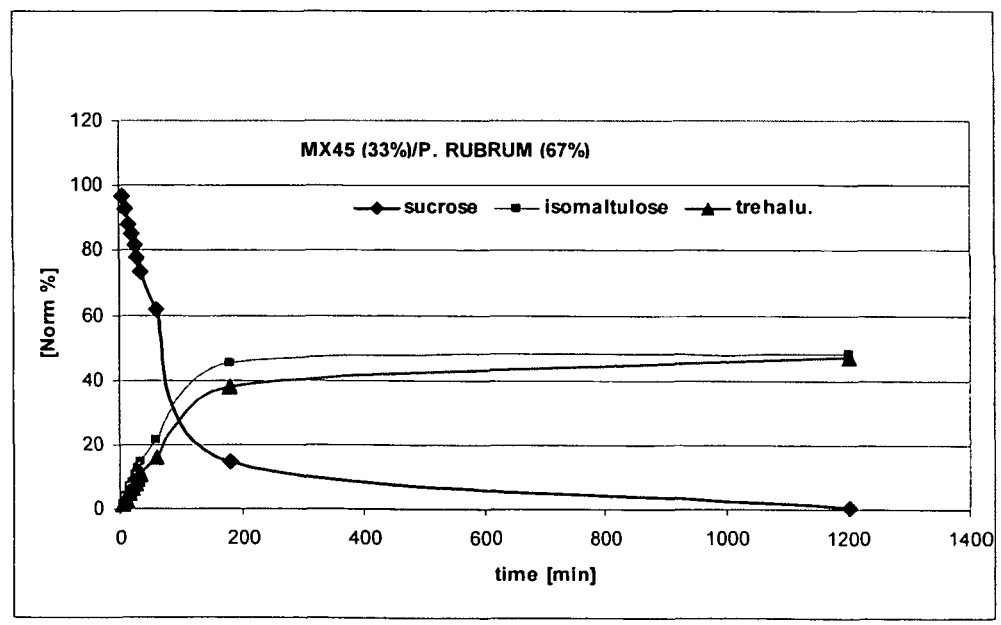
Figure 3:
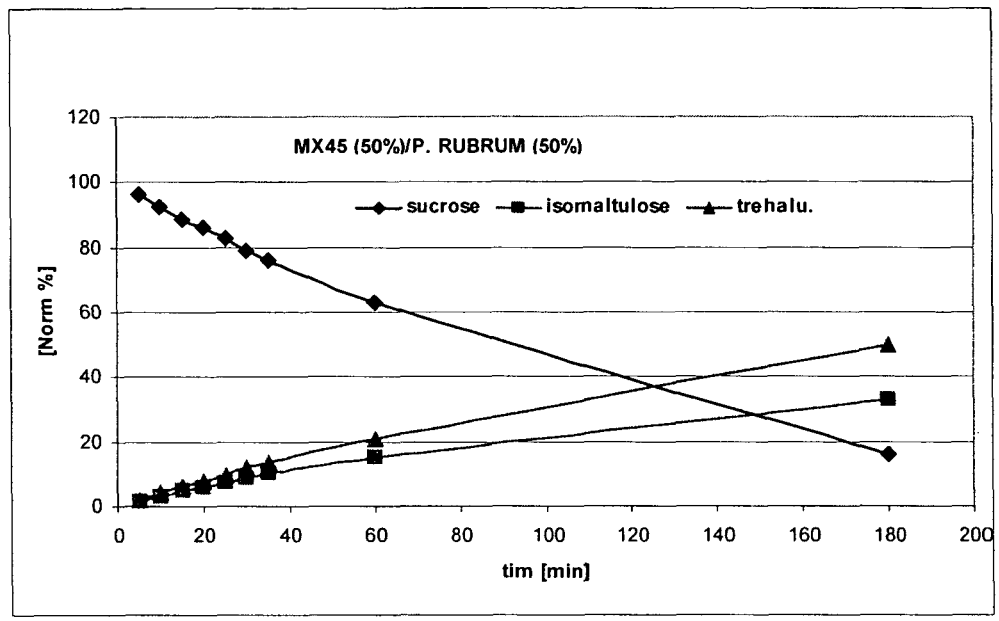
Figure 4:
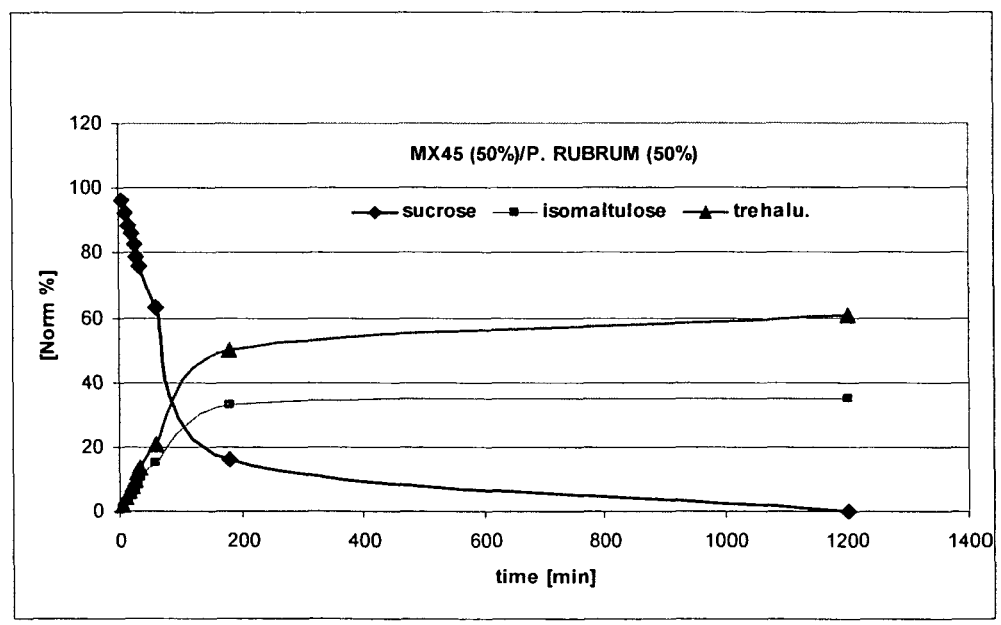
Figure 5:
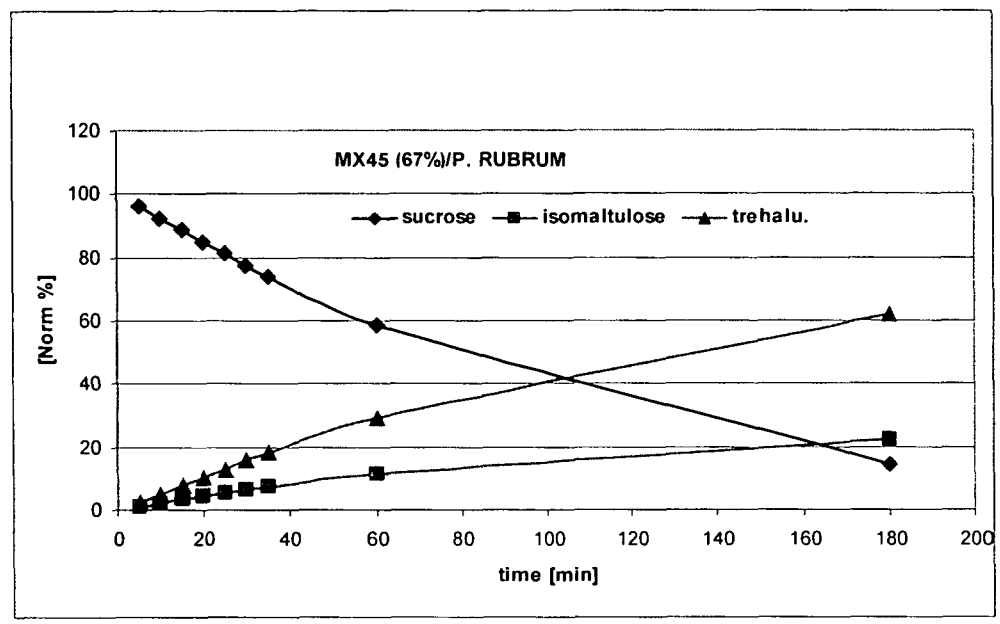
Figure 6:
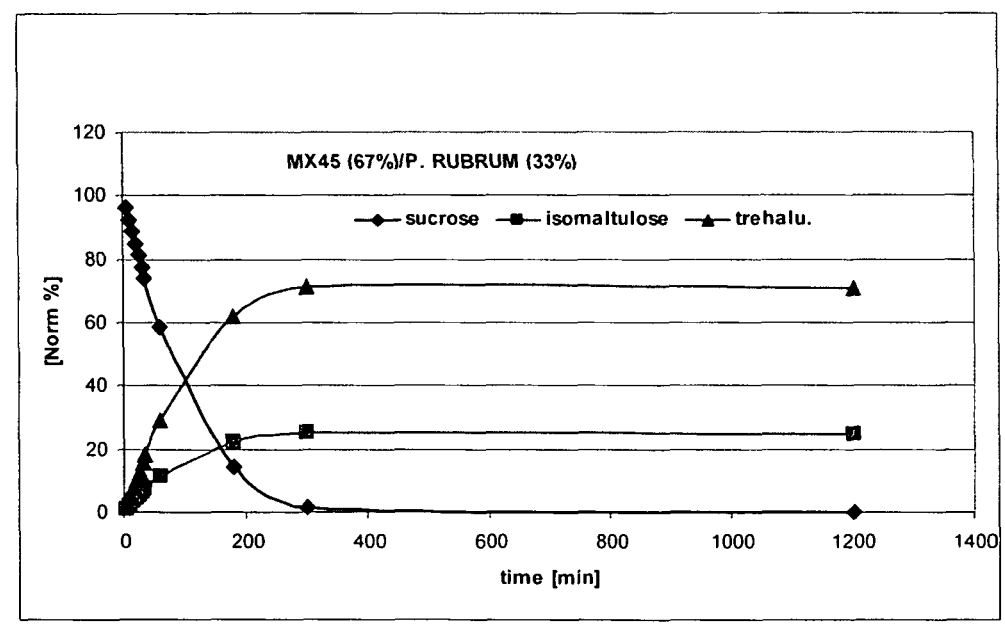
Figure 7:
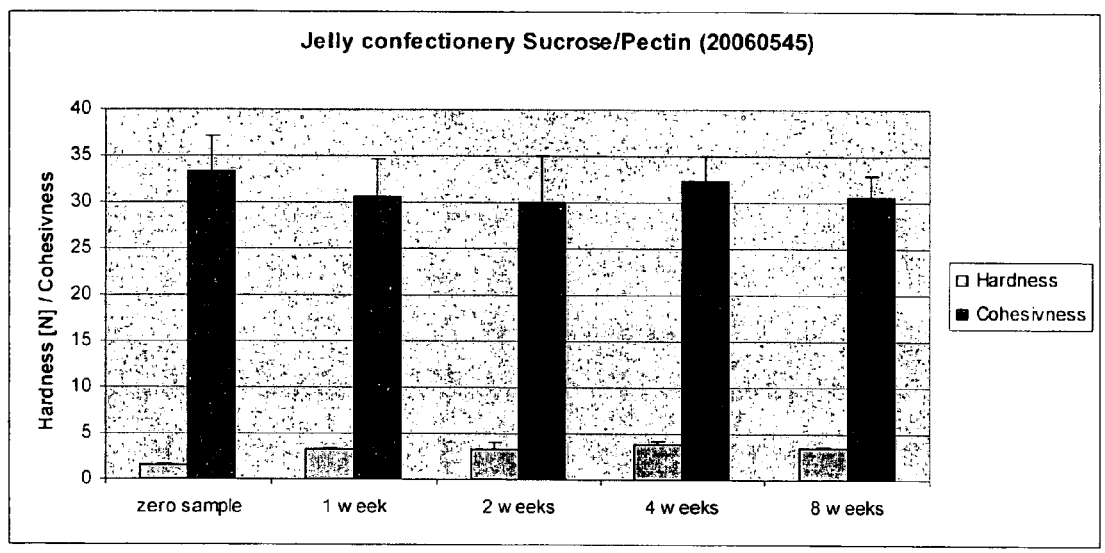
FIGS. 7 to 14 show graphically the hardness and cohesiveness of jellies prepared according to the present invention in comparison to conventional sucrose-based jellies.
Figure 8:
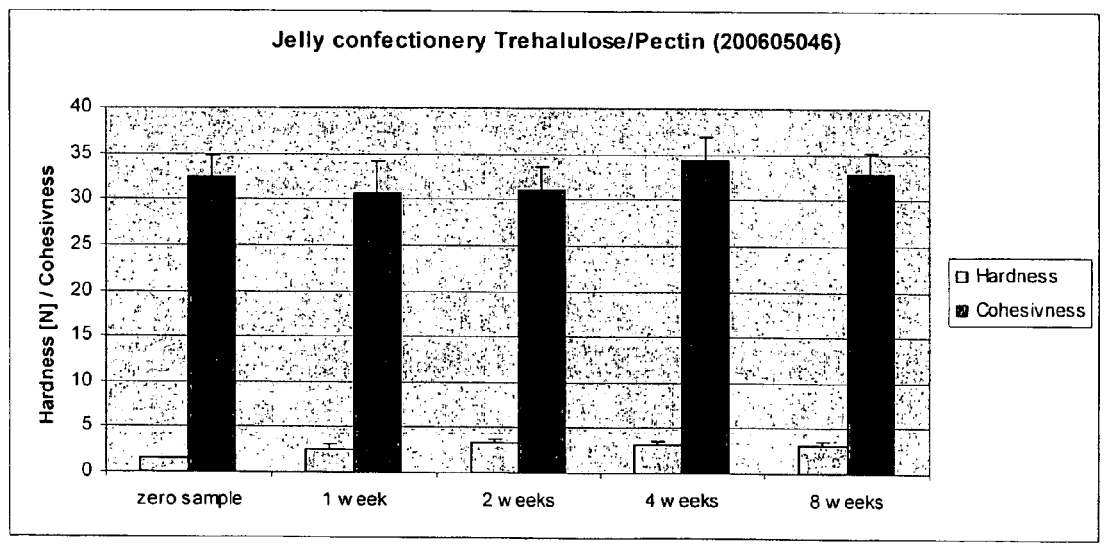
Figure 9:
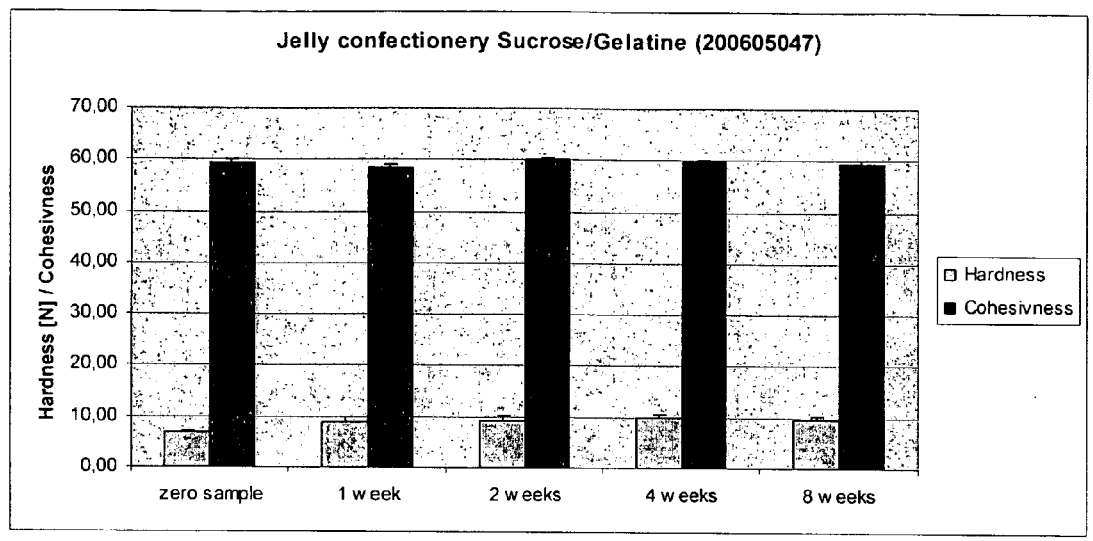
Figure 10:
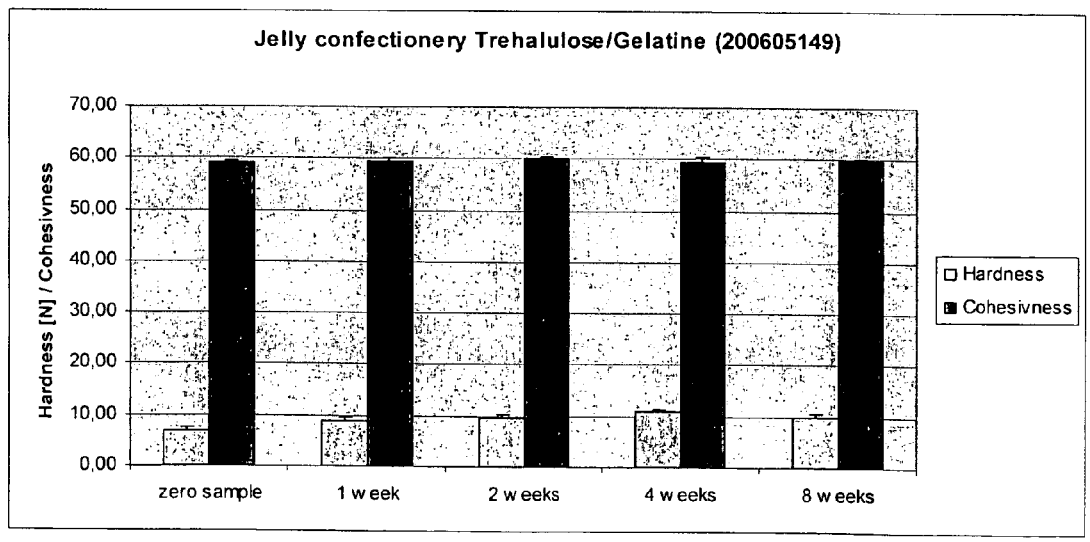
Figure 11:
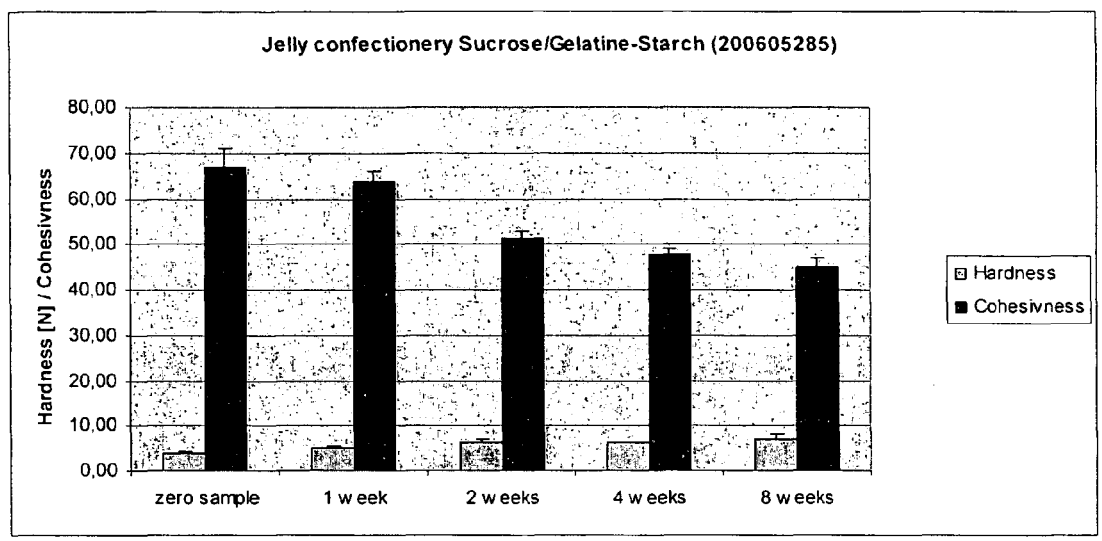
Figure 12:
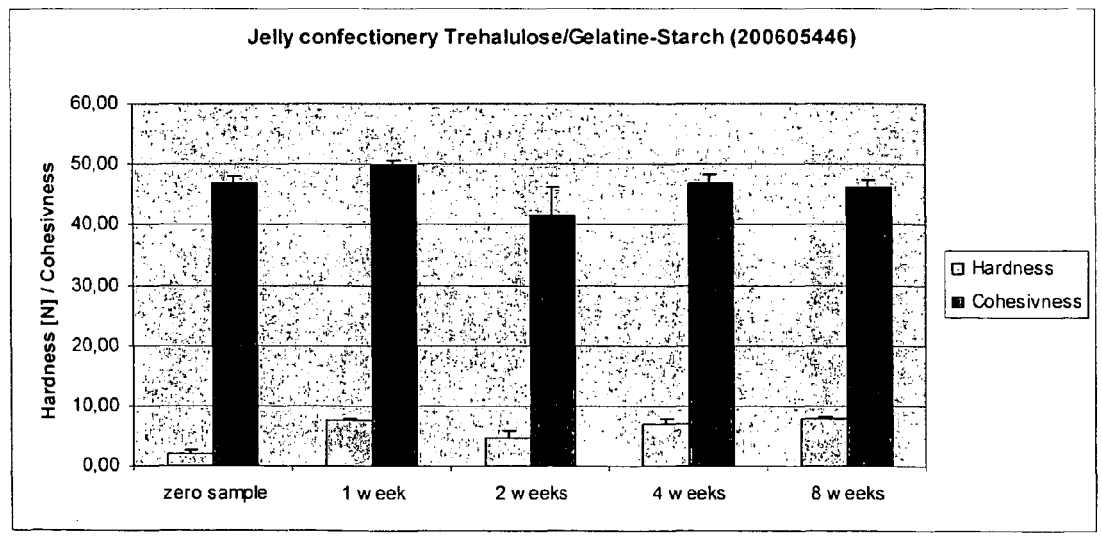
Figure 13:
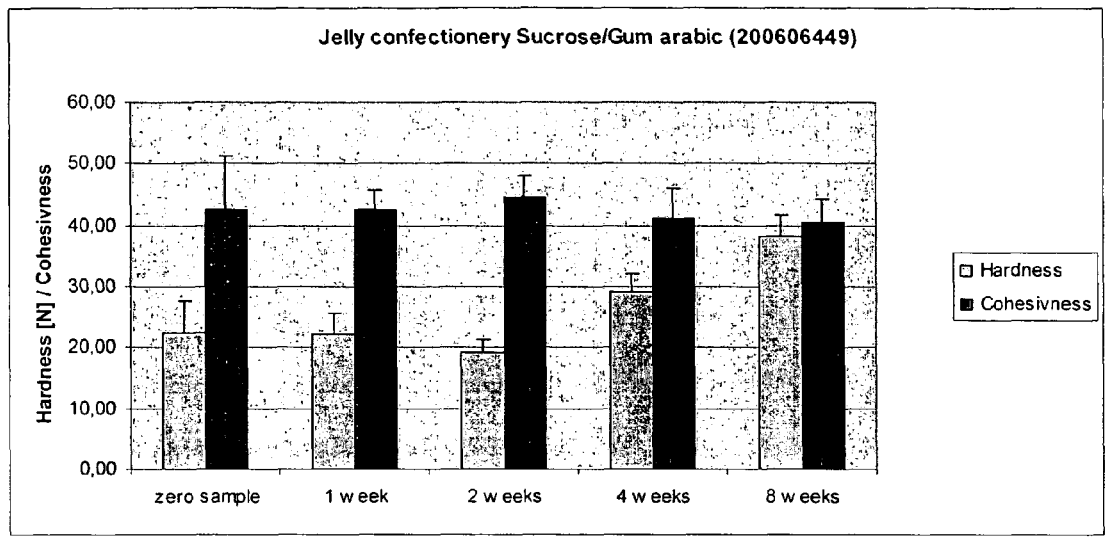
Figure 14:
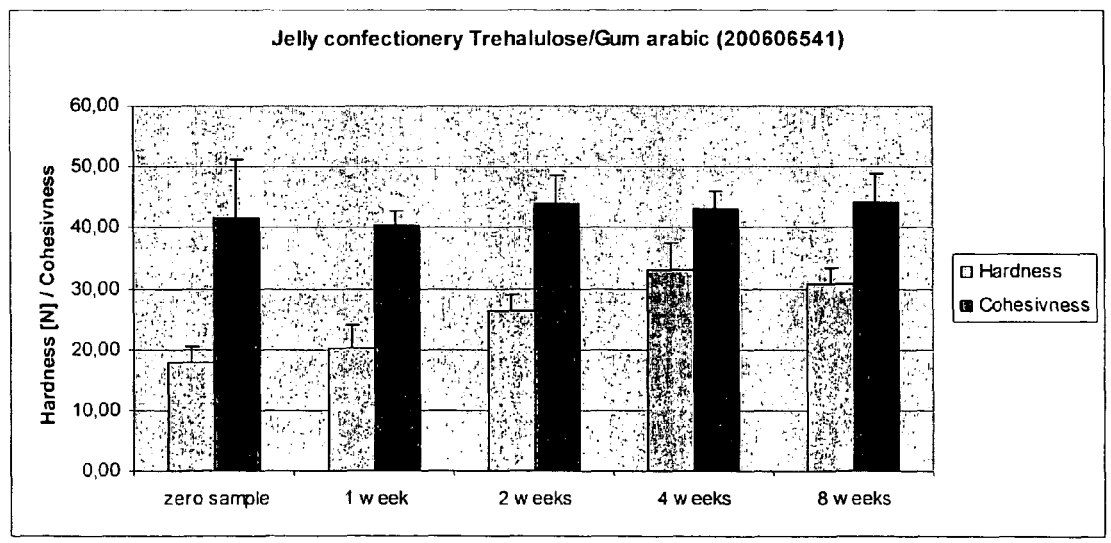

The following examples are provided only for the purpose of illustrating the invention. They are not to be construed in any way as limiting.

Example 1

Preperation of Vitalose

A. Preparation of the *Protaminobacter* Biocatalyst

Cells are rinsed off a subculture of the strain *Protaminobacter rubrum* (CBS 574.77) with 10 ml of a sterile nutrient substrate composed of 8 kg of thick juice from a sugar works (dry matter content 65%), 2 kg of corn steep liquor, 0.1 kg of $(NH_4)_2HPO_4$ and 89.9 kg of distilled water, adjusted to pH 7.2 if required. This suspension is used as inoculum for the shaker preculture in 1 liter flasks containing 200 ml of nutrient solution of the above composition.

After an incubation time of 30 hours at 29° C., 18 liters of nutrient solution of the above composition in a 30 liter small fermenter are inoculated with, in each case, 10 flasks (total content 2 liters) and cultivated at 29° C. with 20 liters of air per minute and a stirrer speed of 350 rpm.

After the organism counts have reached above $5 \times 10^9$ organisms/ml, the cultivation is stopped, the cells are harvested from the fermenter solution by centrifugation, suspended in a 2% strength sodium alginate solution and immobilized by adding the suspension dropwise to a 2% strength calcium chloride solution.

The resulting immobilisate beads are washed with water. This biocatalyst can be stored at +4° C. for several weeks.

B. Preparation of the *Pseudomonas* Biocatalyst

To prepare this biocatalyst, cells were rinsed off a subculture of the strain *Pseudomonas mesoacidophila* MX-45 (FERM BP 3619) with 10 ml of a sterile nutrient substrate composed of 8 kg of thick juice from a sugar works (dry matter content=65%), 2 kg of corn steep liquor, 0.1 kg of $(NH_4)_2HPO_4$ and 89.9 kg of distilled water, adjusted to pH 7.2 if required. This suspension was used as inoculum for a shaker preculture in a 1 liter flask containing 200 ml of the nutrient solution.

After incubation at 29° C. for 30 hours, 18 liters of nutrient solution of the above composition in a 30 liter small fermenter were inoculated with, in each case, 10 flasks (total content 2 liters) and cultivated at 29° C. with 20 liters of air per minute and a stirrer speed of 350 rpm.

After the organism counts had reached above $5 \times 10^9$ organisms/ml, the cultivation was stopped, the cells were harvested from the fermenter solution by centrifugation, suspended in a 2% strength sodium alginate solution and immobilized by adding the suspension dropwise to a 2% strength calcium chloride solution. The resulting immobilisate beads were washed with water. This biocatalyst can be stored at +4° C. for several weeks.

C. Preparation of Vitalose

The immobilized cells obtained as in A) are mixed in a 1:1 weight ratio with the immobilized cells obtained as in B) and are together packed in a column reactor which can be thermostatted and are thermostatted at 25 to 30° C., and a sucrose solution with a DM (dry matter) content of 35 to 45% is passed through continuously. The flow rate in this case is adjusted so that at least 97% of the sucrose employed is converted into the desired trehalulose-containing composition, that means vitalose.

HPLC analysis of the trehalulose-containing composition emerging from the column reactor revealed the following composition:

| | |
|---|---|
| Fructose | 1.0% of DM |
| Glucose | 1.0% of DM |
| Sucrose | 1.0% of DM |
| Isomaltulose | 22.9% of DM |
| Trehalulose | 73.3% of DM |
| Isomaltose | 0.5% of DM |
| Isomelezitose | 0.1% of DM |
| Oligomers (DP > 3) | 0.2% of DM. |

D. Optional Removal of Remaining Sucrose

The remaining sucrose, was, optionally, removed from the trehalulose-containing composition, that means vitalose, obtained in this way by treating it in a strongly acidic cation exchanger loaded with $H^+$ ions or with suitable enzymes in a column reactor as follows:

i) Removal of the Remaining Sucrose on Strongly Acidic Cation Exchangers

100 $cm^3$ of a strongly acidic cation exchanger (for example Lewatit® OC 1052) were packed in a suitable glass column thermostatted at 60° C. and loaded with $H^+$ ions by regeneration with HCl by a known method.

The trehalulose-containing composition, that means vitalose, obtained in Example 1C was pumped at a flow rate of 100 $cm^3 \cdot h^{-1}$ through the cation exchanger column prepared in this way. The product obtained at the column outlet had the following composition (HPLC):

| | |
|---|---|
| Fructose | 1.5% of DM |
| Glucose | 1.5% of DM |
| Sucrose | 0.0% of DM |
| Isomaltulose | 22.9% of DM |
| Trehalulose | 73.3% of DM |
| Isomaltose | 0.5% of DM |
| Isomelezitose | 0.1% of DM |
| Oligomers (DP > 3) | 0.2% of DM | ii) Alternatively, removal of the remaining sucrose was carried out using an immobilized invertase (for example SP 362 from NOVO NORDISK NS Copenhagen). 11 g of said immobilized enzyme corresponding to a bed volume of 33 $cm^3$ was packed in a suitable glass column thermostatted at 60° C.

The trehalulose-containing composition, that means vitalose, obtained in Example 1C was pumped at a flow rate of 210 $cm^3 \cdot h^{-1}$ continuously through this column.

HPLC analysis of the product emerging from the "invertase column" revealed a composition as indicated in section 1D i), above.

In both cases, the remaining sucrose was completely cleaved to glucose and fructose. The content of these monosaccharides was correspondingly higher whereas the other components of the trehalulose-containing composition, that means vitalose, were unchanged.

It is also possible to remove glucose and fructose as well, so as to obtain a completely non-cariogenic sweetener.

Example 2

Sucrose Conversion with Various Ratios of *Pseudomonas* and *Protaminobacter*

In this example, the influence of various ratios of *Pseudomonas mesoacidophila* MX-45 (FERM BP 3619) and *Protaminobacter rubrum* CBS 574.77 on the product composition was analysed.

To prepare the sucrose-containing composition in form of an aqueous medium first solution A was prepared by preparing an aqueous solution of 1.58 g/l calcium acetate (adjusted to a pH of 5.5 with an acetic acid). Then, solution B was prepared by adding solution A up to 1 to 1.4602 mol/l sucrose corresponding to 500 g sucrose.

Both strains of the microorganism, that means *P. mesacidophila* MX-45 and *P. rubrum* CBS 574.77, were cultivated separately as identified in example 1 A and 1 B. After the organism counts each had reached above $5 \times 10^9$ organism/ml, the cultivation of both microorganisms was stopped, the cells were harvested by centrifugation and pooled together in a 2% strength sodium alginate solution and immobilized therefore together by adding the suspension drop wise to a 2% strength calcium chloride solution. The weight ratio employed for combining the both strains of microorganism on the alginate beads prepared thereby is apparent from the below, namely ratios of *Pseudomonas* to *Protaminobacter* of 1:2, 1:1 and 2:1.

5 g of the biocatalyst prepared as indicated was mixed with 50 ml of solution A and kept at room temperature for three hours.

The conversion of the sucrose was started by mixing the suspension of the biocatalyst prepared above in a stirred reactor with 200 ml of the sucrose-containing solution B prepared above at 20° C.

In first set of experiments a biocatalyst was used, wherein from the overall load of microorganism on the carriers 33% was *P. mesoacidophila* MX-45 and 67% *P. rubrum* (% based on weight of the overall microorganism load). In a second set of experiments 50% of the overall microorganism load was MX-45 and 50% *P. rubrum* (% based on weight of the overall microorganism load). In a third set of experiments 67% of the overall load of microorganism was MX-45 and 33% *P. rubrum* (based on weight of the overall microorganism load).

Samples were taken after 5, 10, 15, 20, 25, 30, 35 and 60 minutes, 3 hours and 20.5 hours. The samples taken were cooked, filtrated, diluted to a concentration of 10° Bx (brix, 10 g in 100 g solution) and analysed by HPLC.

The results are given in FIGS. 1 to 6.

From FIGS. 1 to 6 it can be seen that the process of the present invention leads to a complete or almost complete conversion of the sucrose into a trehalulose-containing composition, that means vitalose.

In particular it can be seen that depending up on the specific weight ratio between the cells of the two different microorganism strains immobilized varying ratios of trehalulose to isomaltulose can be obtained. In particular, the more *P. mesoacidophila* is used, the higher the trehalulose content in the product composition is, while the higher the *P. rubrum* proportion, the higher the isomaltulose content in the obtained product is. In particular, the data show that it is possible and highly advantageous to use both microorganism and both enzymatic nutritives simultaneously together for the conversion and that no negative effect on the overall conversion occurred.

Example 3

Preparation of Various Jellies

In the following, four recipes for jellies using as sweeteners a mixture of sucrose and glucose and four recipes using the trehalulose-containing composition, that means vitalose, of the present invention are prepared. The jellies prepared were tested comparatively in storage and TPA-analysis.

3A: Recipes

| | Sample No. | | | | | | | |
|---|---|---|---|---|---|---|---|---|
| | 1 Sucrose/Glucose (240 g dry substance, 41.5%) | 2 Sucrose/Glucose (325 g dry substance, 56%) | 3 Sucrose/Glucose (325 g dry substance, 60%) | 4 Sucrose/Glucose (210 g dry substance, 24%) | 5 Trehalulose (240 g dry substance, 41.5%) | 6 Trehalulose (325 g dry substance, 56%) | 7 Trehalulose (325 g dry substance, 60%) | 8 Trehalulose (250 g dry substance, 24%) |
| Pectin H&F, AF 605 | 13.2 g | | | | 13.2 g | | | |
| Citric acid, anhydrous | 5.0 g | | | 6.0 g | 5.0 g | | | 7.0 g |
| Water | 290.0 g | 104.8 g | 128.8 g | 39.3 g | 232.5 g | 27.0 g | 50.9 g | |
| Sugar | 120.0 g | 162.6 g | 162.6 g | 105.0 g | | | | |
| Glucose syrup DE 42 (approx. 80% dry substance) | 150.0 g | 203.2 g | 203.2 g | 131.3 g | | | | |
| Trehalulose (73.3% dry substance) | | | | | 327.5 g | 443.5 g | 443.7 g | |
| Trehalulose (73.1% dry substance) | | | | | | | | 344.7 g |
| Lemon aroma | 0.4 g | 0.4 g | 0.4 g | 0.5 g | 0.4 g | 0.4 g | 0.4 g | 0.6 g |
| Gelatine (280 Bloom) | | 35.0 g | 18.0 g | | | 35.0 g | 18.0 g | |

-continued

| | Sample No. | | | | | | | |
|---|---|---|---|---|---|---|---|---|
| | 1<br>Sucrose/<br>Glucose<br>(240 g dry<br>substance,<br>41.5%) | 2<br>Sucrose/<br>Glucose<br>(325 g dry<br>substance,<br>56%) | 3<br>Sucrose/<br>Glucose<br>(325 g dry<br>substance,<br>60%) | 4<br>Sucrose/<br>Glucose<br>(210 g dry<br>substance,<br>24%) | 5<br>Trehalulose<br>(240 g dry<br>substance,<br>41.5%) | 6<br>Trehalulose<br>(325 g dry<br>substance,<br>56%) | 7<br>Trehalulose<br>(325 g dry<br>substance,<br>60%) | 8<br>Trehalulose<br>(250 g dry<br>substance,<br>24%) |
| Water for gelatine | | 60.0 g | | | | 60.0 g | | |
| Citric acid solution, 50% | | 10.0 g | 10.0 g | | | 10.0 g | 10.0 g | |
| Starch purity gum 400 | | | 18.0 g | | | | 18.0 g | |
| Gum arabic solution (52.9%) | | | | 600.0 g | | | | 720.0 g | legend:
Sample no. 1 to 4: sucrose/glucose compositions
Sample no. 5 to 8: vitalose (trehalulose-containing composition) of the present invention Composition of Sample 5 to 8:

| Sample No. | | water content (Karl Fischer-method) | fructose | glucose | sucrose | isomaltulose | trehalulose | isomaltose | DP-3 | isomelezitose | remainder |
|---|---|---|---|---|---|---|---|---|---|---|---|
| | | | | | | g/100 g | | | | | |
| | | titrim. | | | | HPLC-NH2 | | | | | |
| 5 | TREHALULOSE/<br>PECTINE | 44.5 | 0.1 | 0.2 | <0.1 | 4.6 | 41.2 | 0.1 | <0.1 | <0.1 | 0.2 |
| 6 | TREHALULOSE/<br>GELATINE | 21.2 | 0.2 | 0.3 | <0.1 | 7.3 | 63.9 | 0.2 | <0.1 | <0.1 | 0.4 |
| 7 | TREHALULOSE/<br>GELATINE/<br>STARCH | 17.1 | 0.2 | 0.2 | <0.1 | 7.5 | 67.4 | 0.2 | <0.1 | <0.1 | 0.4 |
| 8 | TREHALULOSE/<br>GUM ARABIC | 22.7 | 0.3 | 0.3 | <0.1 | 2.5 | 16.2 | <0.1 | <0.1 | <0.1 | 3 |

3 B. TPA-Analysis

In a comparative testing the samples prepared in example 3 A, above, were analysed in detail, i.e. the sucrose/glucose compositions containing various thickeners (pectin, gelatine, starch and/or gum arabic) were compared to the trehalulose-containing compositions, that means vitalose.
i) TPA-Analysis (Hardness, Cohesiveness)
ii) Storage in Closed PE (Polyethylene)-Bags at 25° C. for 8 Weeks The intervals of analysis for the TPA tests and the storage behaviour were done after O (begin of storage), 1, 2, 4, 8 weeks.

In all of the jelly recipes the conventional sweetener combination of sucrose and glucose could be successfully replaced by the trehalulose-containing composition, that means vitalose, of the present invention. The preparation using the trehalulose-containing composition, that means vitalose, was exactly as for the sucrose/glucose compositions. During the preparation, in particular when cooking the jellies, no degradation of trehalulose was observed.

As is evident from the results given in the FIGS. 7 to 14, the TPA measurements of hardness and cohesiveness show that the jellies made from the trehalulose-containing composition, that means vitalose, of the present invention are equal or very similar to the conventional sucrose/glucose based products. The storage behaviour was also comparable. Storage at refrigerator temperatures, that means 7° C., showed a particular good stability and prolonged shelf life.

Thus, these results show that both in terms of preparation and product characteristics the present trehalulose-containing composition, that means vitalose, can be used instead of the conventionally used sucrose/glucose sweeteners in jellies, but in addition provide the advantages mentioned herein, namely the specific physiological and nutritional advantages in regard of the glycemic and insulinemic behaviour.

Example 4

Preparation of Various Products with the Trehalulose-Containing Composition, that Means Vitalose, of the Present Invention 4.1) Cereal Bar

| | Trehalulose - Raftilose ® bars | Amount [g] |
|---|---|---|
| | Trehalulose syrup<br>(73.1% dry substance, see example 3) | |
| 12% | "trehalulose"* | 60.00 |
| 4.42% | water | 22.08 |
| 16.58% | Water (desalted) | 82.92 |
| 21% | Oligofructose P95 (Orafti) (Raftilose ®) | 105.00 |
| 8% | Fat Toffix P (Sasol) | 40.00 |
| 1.9% | Emulgent Dimodan HP (Danisco) | 9.50 |

-continued

| | Trehalulose - Raftilose ® bars | Amount [g] |
|---|---|---|
| 10% | Lactoprotein, Promilk 852 A1 (Ingredia) | 50.00 |
| 0.05% | Ascorbic acid powder Reinst (Fluka) | 0.25 |
| 0.05% | Vitamine mixture (Dohler) | 0.25 |
| 10% | Desiccated coconut, Backfee | 50.00 |
| 8% | Chopped almonds, Backfee | 40.00 |
| 8% | Whole grain oat meal (Kolln) | 40.00 |
| 100% | In total | 500.00 |

*Here "Trehalulose" refers to a 90:10 trehalulose/isomaltulose mixture.

4.2) Hard Candies (Units in Weight-%)

| components | A* | B* |
|---|---|---|
| Trehalulose-containing compostion (ex. 1D) | 92.34 | 92.34 |
| Reb A# | 0.06 | 0.06 |
| Citric acid | — | 1.55 |
| Herbal essence | 0.78 | — |
| Flavouring agent | 0.04 | 0.04 |
| Flavouring agent (herbal flavour) | 0.12 | — |
| Lactobionic acid | 0.12 | 0.12 |
| Colouring agent | 0.66 | 0.01 |
| Water | 5.88 | 5.88 | ex: example
Reb A content >97 weight-% on dry matter of total Reb A sweetener
*A: throat lozenge
*B: lemon candy 4.3) Ice Cream (Units in Weight-%)

| components | |
|---|---|
| Trehalulose-containing composition (ex. 1D) | 22.17 |
| Reb A# | 0.04 |
| Lactobionic acid | 0.90 |
| Skim milk (sugar content 53%) | 8.07 |
| butter (milk fat 82%) | 10.09 |
| Emulsifying agent | 0.30 |
| Stabilizer | 0.22 |
| Flavouring agent | 0.20 |
| Colouring agent | 0.02 |
| Milk fat | 8.25 |
| Milk solids | 16.21 |
| Water | 57.99 |

: ≥95 weight-% of Reb A, rebaudioside B, rebaudioside C, dulcoside A, stevioside, rubusoside and steviolbioside on dry matter of total Reb A sweetener 4.4) Canned Orange (Units in Weight-%)

| components | |
|---|---|
| Trehalulose-containing composition (ex. 1C) | 11.00 |
| Orange pulp | 67.80 |
| Citric acid | 0.40 |
| Water | 20.80 |

4.5) Carrot Juice (Units in Weight-%)

| components | |
|---|---|
| Trehalulose-containing composition (ex. 1D) | 10.70 |
| Carrot juice | 30.00 |
| Citric acid | 0.05 |
| Flavouring agent | 0.10 |
| Water | 59.15 |

4.6) Fondant (Units in Weight-%)

| Components | |
|---|---|
| Trehalulose-containing composition (ex. 1D) | 97.8 |
| Water | 2.2 |

Example 5

Sweetening Power

To establish the relative sweetening power, the following solutions were compared with one another in a triangle test with 15 testers in each case:

a) Two 7% strength sucrose solutions versus a 15.5% strength solution of the sweetener according to example 1D.

b) Two 7% strength sucrose solutions versus a 17.5% strength solution of the sweetener according to example 1D.

c) Two 7% strength sucrose solutions versus an 18.5% strength solution of the sweetener according to example 1D.

In test a), six people identified the sweetener: no statistically verified difference from the sucrose solutions.

In test b), twelve people identified the present sweetener as "sweeter": statistically verified difference with p=0.99.

In test c), likewise twelve people identified the present sweetener as "sweeter": statistically verified difference with p=0.99.

The sweetening power of the sweetener according to the invention is about half of that of sucrose. To increase the sweetening power, the sweetener can be mixed with for instance Reb A and lactobionic acid.

Example 6

Ice Cream

To produce ice cream with the sweetener of example 1D, 22.1 kg of dairy cream (40% fat in dry matter), 58.1 kg of whole milk (3.7% fat in DM) and 4.5 kg of skim milk powder were mixed with 15 kg of the sweetener of example 1D and 0.3 kg of stabilizer, homogenized and sterilized.

After the sterilization, 53 g of finely ground methyl phenylalanylaspartate were added to the ice composition, stirred, whipped and frozen. The product has the same sweetness and the same taste as ice cream produced with 15 kg of sugar.

In the case of fruit ice cream it may be particularly advantageous to dispense with additional sweeteners, such as Reb A, because the sweetener brings out the taste of the fruit considerable better.

Example 7

Strawberry Jam

To produce a low-calorie strawberry jam, 1 kg of chopped strawberries was boiled together with 1 kg of the sweetener of example 1C and 8 g of a medium-esterified pectin and 7 g of tartaric acid for three minutes and bottled in prepared bottles.

Comparison with a jam produced with sucrose showed no difference in consistency, the sweetness was somewhat less but this was compensated by the strawberry taste being detectably stronger. After storage for a period of six months, the sweetener showed no tendency to crystallize.

Example 8

The effect of trehalulose on the blood glucose response (glycemic index, GI) and the insulin response (insulinemic index, II) was examined in comparison to isomaltulose.

The analysis was done as a randomized cross over analysis on ten healthy subjects of both sex.

Blood glucose- and insulin-profiles were taken after consumption of isomaltulose or trehalulose (each 25 g carbohydrate and 250 ml water) for an interval of 0 to 180 minutes at the following time points 0, 15, 30, 45, 60, 90, 120, 150 and 180 minutes.

Figure 15:
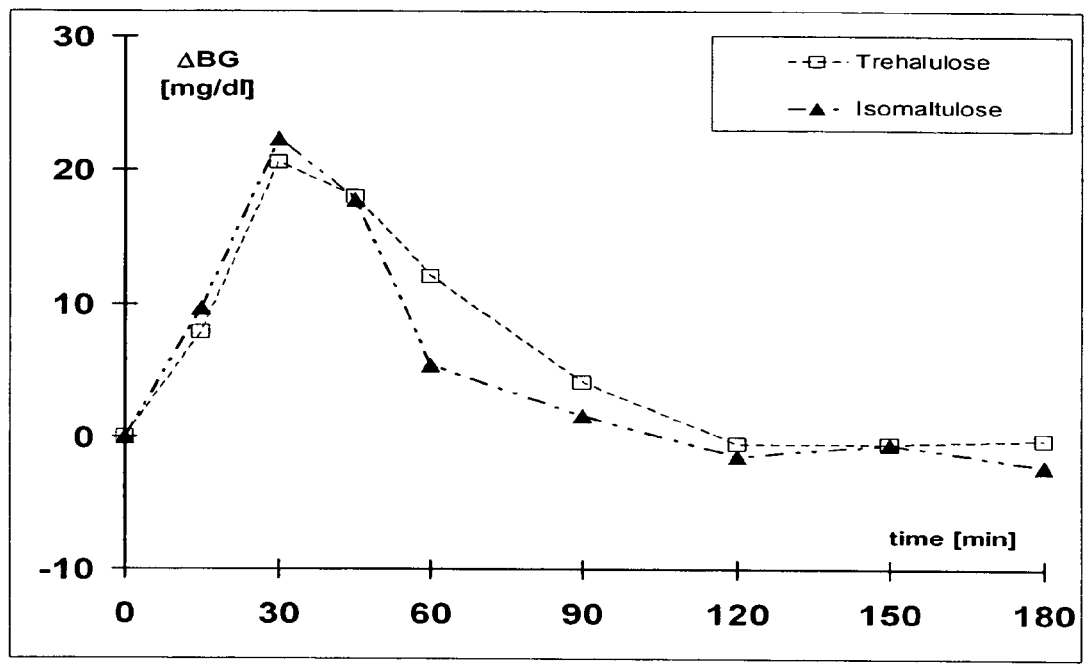
FIG. 15 shows the blood glucose level of a consumer after consumption of isomaltulose and trehalulose and FIG. 16 shows the blood insulin level of a consumer after consumption of isomaltulose and trehalulose.
Figure 16:
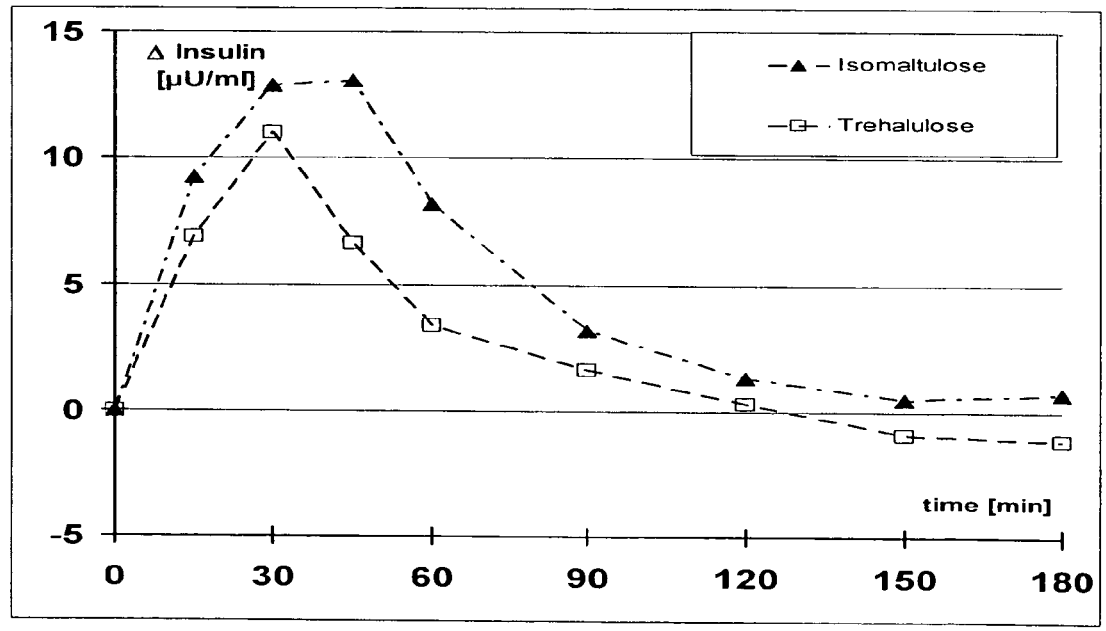

The results are given in FIGS. 15 and 16. As the graph for the blood glucose level for trehalulose shows, trehalulose provides an increased and longer sustaining supply of glucose (GI), which is a supply longer and in sum greater than provided by isomaltulose.

The insulin response (II) of isomaltulose runs, as expected on the basis of the blood glucose response of isomaltulose, in parallel to the blood glucose response. In contrast, trehalulose shows a significantly lower insulin response (II) than isomaltulose and a significantly lower blood insulin level in contrast to what has been expected by the blood glucose response of trehalulose. Thus, trehalulose provides a longer, more sustained and greater blood glucose level than isomaltulose and simultaneously provides unexpectedly a significantly lower insulin response compared to isomaltulose, which is also lower than expected considering the blood glucose profile of trehalulose itself.

What is claimed is:

1. A beverage comprising at least 70 weight-% of a trehalulose-containing composition, based on the total weight of the beverage, wherein the trehalulose-containing composition comprises a trehalulose content of 35 to 65 weight, the remainder of the composition adds up to 100% with isomaltulose or isomaltulose and 0.1 to 4 weight-% of minor components, which minor components are isomaltulose, isomelezitose, carbohydrate oligomers with a DP (degree of polymerization) greater than or equal to 3, glucose, fructose and/or sucrose, each based on dry matter of the trehalulose-containing composition, and wherein the beverage does not crystallize.

2. The beverage of claim 1 wherein the trehalulose-containing composition comprises 0.1 to 2.0 weight-% fructose based on dry matter of the trehalulose-containing composition.

3. The beverage according to claim 1 wherein the trehalulose-containing composition comprises 0.1 to 0.4 weight-% glucose based on dry matter of the trehalulose-containing composition.

4. The beverage according to claim 1 wherein the trehalulose-containing composition comprises 0.1 to 0.4 weight-% fructose based on dry matter of the trehalulose-containing composition.

5. The beverage according to claim 1, wherein the beverage further comprises at least one additive.

6. The beverage according to claim 5, wherein the beverage comprises 0.02 to 3.0 weight-% of the at least one additive and 97.0 to 99.98 weight-% of the trehalulose-containing composition based on dry matter.

7. The beverage according to claim 5, wherein the additive is at least one of a stevia extract and a steviolglycoside.

8. The beverage according to claim 5, wherein the additive is selected from the group consisting of acidic flavours, fruit flavours, sweet flavours, savoury flavours, salty flavours, a high intensity sweetener, a sugar alcohol, sucromalt, ribose, tagatose, trehalose, organic acid, fruit extract, a bulk sweetener, a fibre, a prebiotic agent, a thickener, a vitamin, a mineral, a preservative, a food colour, and a therapeutic agent, or wherein the additive is selected from the group consisting of creatine, polyphenole, L-carnitin, omega-3 polyunsaturated fatty acid, omega-6 polyunsaturated fatty acid, green tea extract, EGCG (epigallocatechingallate), aminoacids and peptropro.

9. The beverage according to claim 5, wherein the additive is a tryptophan-containing peptide composition.

10. The beverage according to claim 5, which is a food, an animal feed or a pharmaceutical product.

11. A method for preparing a beverage for human or animal consumption, said product being capable of and designed for a sustained release of glucose and for simultaneously eliciting a low insulin response, wherein said method comprises including in said beverage at least 70 weight-% of the trehalulose-containing composition according to claim 1.

12. The method of claim 11 wherein the beverage is a pharmaceutical product.

13. A method for the preparation of a beverage comprising at least 70 weight-% of a trehalulose-containing composition according to claim 1, based on the total weight of the beverage, wherein: (a) a sucrose-containing composition is contacted at a temperature of from 10° to 40° C. with cells or cell extracts from microorganisms of the genera *Pseudomonas* and *Protaminobacter*, wherein the cells or cell extracts of both genera of microorganisms are co-immobilized on the same carrier, and (b) the trehalulose-containing composition is produced, wherein the beverage does not crystallize.

14. The method according to claim 13, wherein the sucrose-containing composition is dissolved or suspended in an aqueous medium.

15. The method according to claim 13, wherein the cells or the cell extracts are immobilized on at least one carrier.

16. The beverage according to claim 1, wherein the trehalulose-containing composition comprises 0.1 to 2.0 weight-% glucose, based on the dry matter of the trehalulose-containing composition.

* * * * *

UNITED STATES PATENT AND TRADEMARK OFFICE
CERTIFICATE OF CORRECTION

PATENT NO. : 9,744,184 B2  
APPLICATION NO. : 13/263361  
DATED : August 29, 2017  
INVENTOR(S) : Wolfgang Wach et al.

Page 1 of 1

It is certified that error appears in the above-identified patent and that said Letters Patent is hereby corrected as shown below:

In the Claims

In Claim 1, at Column 25, Line 41, "isomaltulose" should read -- isomaltose --.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*